(12) United States Patent
Burns et al.

(10) Patent No.: US 11,426,381 B2
(45) Date of Patent: *Aug. 30, 2022

(54) LIPOIC ACID CHOLINE ESTER COMPOSITIONS AND METHODS OF USE

(71) Applicant: NOVARTIS AG, Basel (CH)

(72) Inventors: William Burns, North Richland Hills, TX (US); Margaret Garner, Eastport, ME (US); William H. Garner, Eastport, ME (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/578,368

(22) Filed: Sep. 22, 2019

(65) Prior Publication Data
US 2020/0281891 A1 Sep. 10, 2020

Related U.S. Application Data

(63) Continuation of application No. 15/118,910, filed as application No. PCT/US2015/018505 on Mar. 3, 2015, now abandoned.

(60) Provisional application No. 61/947,378, filed on Mar. 3, 2014.

(51) Int. Cl.
*A61K 31/385* (2006.01)
*A61K 47/10* (2017.01)
*A61K 9/08* (2006.01)
*A61K 47/18* (2017.01)
*A61K 9/00* (2006.01)

(52) U.S. Cl.
CPC .......... *A61K 31/385* (2013.01); *A61K 9/0048* (2013.01); *A61K 9/08* (2013.01); *A61K 47/10* (2013.01); *A61K 47/183* (2013.01); *A61K 47/186* (2013.01)

(58) Field of Classification Search
CPC .. A61K 31/385; A61K 47/186; A61K 47/183; A61K 47/10; A61K 9/0048; A61K 9/06
See application file for complete search history.

(56) References Cited

U.S. PATENT DOCUMENTS

| | | |
|---|---|---|
| 3,238,224 A | 3/1966 | Ohara et al. |
| 3,855,240 A | 12/1974 | Mueller |
| 4,210,667 A | 7/1980 | Sarges et al. |
| 4,755,528 A | 7/1988 | DuPriest et al. |
| 5,395,356 A | 3/1995 | King et al. |
| 5,459,133 A | 10/1995 | Neufeld |
| 5,465,737 A | 11/1995 | Schachar |
| 5,466,680 A | 11/1995 | Rudy |
| 5,476,515 A | 12/1995 | Kelman et al. |
| 5,488,050 A | 1/1996 | Neufeld |
| 5,503,165 A | 4/1996 | Schachar |
| 5,527,774 A | 6/1996 | Giard |
| 5,529,076 A | 6/1996 | Schachar |
| 5,624,955 A | 4/1997 | Nagasawa et al. |
| 5,665,770 A | 9/1997 | Terao et al. |
| 5,686,450 A | 11/1997 | Hellberg et al. |
| 5,688,828 A | 11/1997 | Hellberg et al. |
| 5,691,379 A | 11/1997 | Ulrich et al. |
| 5,722,952 A | 3/1998 | Schachar |
| 5,817,630 A | 10/1998 | Hofmann et al. |
| 5,843,184 A | 12/1998 | Cionni |
| 5,869,468 A | 2/1999 | Freeman |
| 5,874,455 A | 2/1999 | Terao et al. |
| 5,888,243 A | 3/1999 | Silverstrini |
| 6,007,510 A | 12/1999 | Nigam |
| 6,013,462 A | 1/2000 | Kauvar et al. |
| 6,030,950 A | 2/2000 | Ohlenschlager |
| 6,063,116 A | 5/2000 | Kelleher |
| 6,153,647 A | 11/2000 | Mallet et al. |
| 6,214,044 B1 | 4/2001 | Silverstrini |
| 6,273,092 B1 | 8/2001 | Nolan |
| 6,288,106 B1 | 9/2001 | Pearson et al. |
| 6,313,164 B1 | 11/2001 | Fujita et al. |
| 6,339,102 B1 | 1/2002 | Meyerhoff et al. |
| 6,387,945 B2 | 5/2002 | Packer et al. |
| 6,472,541 B2 | 10/2002 | Tslen et al. |
| 6,484,874 B1 | 11/2002 | Kageyama et al. |
| 6,654,287 B2 | 12/2003 | Avery et al. |
| 6,703,039 B2 | 3/2004 | Xia et al. |
| 6,743,779 B1 | 6/2004 | Unger et al. |

(Continued)

FOREIGN PATENT DOCUMENTS

| | | |
|---|---|---|
| EP | 0 369 880 | 5/1990 |
| EP | 2 179 736 A1 | 4/2010 |

(Continued)

OTHER PUBLICATIONS

Al-Ghoul, K. J., R. K. Nordgren, A. J. Kuszak, C. D. Freel, M. J. Costello, and J. R. Kuszak, 2001. Structural evidence of human nuclear fiber compaction as a function of ageing and cataractogenesis. Experimental eye research 72: 199-214.

Applegate, M. A., K. M. Humphries, and L. J. Szweda, Jan. 2007. Reversible Inhibition of alpha-Ketoglutarate Dehydrogenase by Hydrogen Peroxide: Glutathionylation and Protection of Lipoic Acid. Biochemistry. 47(1): 473-478.

Argirova, M., M. Kleine-Reidick, and W. Breipohl, 2004. Redox status of the eye lens: a regional study. Cell biochemistry and biophysics 41: 381-390.

Ariga T, et al. 2000. Antithrombotic and antieoplastic effects of phyto-organosulfur compounds. Biofactors. 13(1-4):251-5.

(Continued)

*Primary Examiner* — Shobha Kantamneni
(74) *Attorney, Agent, or Firm* — Sophie Binet Cross

(57) ABSTRACT

Provided herein are pharmaceutical compositions comprising a therapeutically effective amount of lipoic acid choline ester or derivatives thereof and a non-aqueous excipient mixed in an aqueous solution. Also provided herein are non-aqueous compositions prepared by mixing the therapeutically effective amount of lipoic acid choline ester and the non-aqueous excipient. The non-aqueous compositions can be further mixed with the aqueous solution.

9 Claims, 5 Drawing Sheets

(56) References Cited

U.S. PATENT DOCUMENTS

| | | |
|---|---|---|
| 6,923,955 B2 | 8/2005 | Till et al. |
| 7,164,943 B2 | 1/2007 | Roy |
| 7,718,697 B2 | 5/2010 | Drace et al. |
| 7,914,815 B2 | 3/2011 | Till et al. |
| 7,935,332 B2 | 5/2011 | Till |
| 8,147,816 B2 | 4/2012 | Till et al. |
| 8,410,162 B2 | 4/2013 | Garner et al. |
| 8,410,462 B2 | 4/2013 | Brutschin et al. |
| 8,647,612 B2 | 2/2014 | Garner et al. |
| 8,697,109 B2 | 4/2014 | Garner et al. |
| 8,747,829 B2 | 6/2014 | Till et al. |
| 8,795,706 B2 | 8/2014 | Garner et al. |
| 9,044,439 B2 | 6/2015 | Garner et al. |
| 9,161,931 B2 | 10/2015 | Garner et al. |
| 9,204,996 B2 | 12/2015 | Till et al. |
| 9,284,305 B2 | 3/2016 | Garner et al. |
| 9,326,970 B2 | 5/2016 | Garner et al. |
| 2002/0025311 A1 | 2/2002 | Till |
| 2002/0035243 A1 | 3/2002 | Imfeld et al. |
| 2003/0187058 A1 | 10/2003 | Hasselwander et al. |
| 2003/0228299 A1 | 12/2003 | Droy-Lefaix et al. |
| 2004/0044227 A1 | 3/2004 | Klatt et al. |
| 2004/0092586 A1 | 5/2004 | Ogata et al. |
| 2005/0101677 A1 | 5/2005 | Till |
| 2005/0112113 A1 | 5/2005 | Till et al. |
| 2005/0130881 A1 | 6/2005 | Shashoura et al. |
| 2005/0137123 A1 | 6/2005 | Drace et al. |
| 2005/0137124 A1 | 6/2005 | Castillejos |
| 2005/0171212 A1 | 8/2005 | Gierhart et al. |
| 2005/0287201 A1 | 12/2005 | Till et al. |
| 2006/0177430 A1 | 8/2006 | Bhushan |
| 2006/0188492 A1 | 8/2006 | Richardson et al. |
| 2006/0275278 A1 | 12/2006 | Choy et al. |
| 2007/0055070 A1 | 3/2007 | Lawrence |
| 2007/0099845 A1 | 5/2007 | Sheu et al. |
| 2007/0207116 A1 | 9/2007 | Brown |
| 2007/0293562 A1 | 12/2007 | Mylari et al. |
| 2008/0038316 A1 | 2/2008 | Wong et al. |
| 2008/0139990 A1 | 6/2008 | Till et al. |
| 2008/0213239 A1 | 9/2008 | Morris |
| 2009/0082281 A1 | 3/2009 | Shashoua |
| 2009/0093541 A1 | 4/2009 | Ogata |
| 2009/0192212 A1 | 7/2009 | Garner et al. |
| 2010/0098653 A1 | 4/2010 | Yu et al. |
| 2010/0317608 A1 | 12/2010 | Garner et al. |
| 2010/0317725 A1 | 12/2010 | Garner et al. |
| 2011/0135622 A1 | 6/2011 | Till et al. |
| 2013/0046014 A1 | 2/2013 | Theisinger |
| 2014/0121266 A1 | 5/2014 | Garner et al. |
| 2014/0243385 A1 | 8/2014 | Garner et al. |
| 2014/0336562 A1 | 11/2014 | Till et al. |
| 2014/0357691 A1 | 12/2014 | Garner et al. |
| 2015/0297561 A1 | 10/2015 | Garner et al. |
| 2016/0264545 A1 | 9/2016 | Garner et al. |

FOREIGN PATENT DOCUMENTS

| | | |
|---|---|---|
| JP | H08511246 A | 11/1996 |
| WO | WO 93/25166 | 12/1993 |
| WO | WO 93/25199 | 12/1993 |
| WO | WO 94/01773 | 1/1994 |
| WO | WO 0203863 | 2/2002 |
| WO | WO 02/056804 | 7/2002 |
| WO | WO 2003/084532 | 10/2003 |
| WO | WO 2004/028536 | 4/2004 |
| WO | WO 2005/084635 | 9/2005 |
| WO | WO 2006/017080 | 5/2006 |
| WO | WO 07/011874 | 1/2007 |
| WO | WO 2008/120070 | 10/2008 |
| WO | WO 10/054135 | 5/2010 |
| WO | WO 10/147962 | 12/2010 |
| WO | 2011/104037 A2 | 9/2011 |
| WO | WO 2012/093113 A1 | 7/2012 |
| WO | WO 2013/110621 A | 8/2013 |
| WO | WO 2013/126597 A1 | 8/2013 |

OTHER PUBLICATIONS

Arora A, et al. 2004. Reversal of P-glycoprotein-mediated multidrug resistance by diallyl sulfide in K562 leukemic cells and in mouse liver. Carcinogenesis. 25(6):941-9. Epub Jan. 16, 2004.

Asmellash S, et al. 2005. Modulating the endoplasmic reticulum stress response with trans-4,5-dihydroxy-1,2-dithiane prevents chemically induced renal injury in vivo. Toxicol Sci. 88(2):576-84. Epub Sep. 8, 2005.

Baghieri, S., and M. H. Garner. 1992. Na,K-ATPase and phospholipid degradation in bovine and human lenses. Current eye research 11: 459-467.

Belloir C, et al. 2006. Protective effect of garlic sulfur compounds against DNA damage induced by direct- and indirect-acting genotoxic agents in HepG2 cells. Food Chem Toxicol. 44(6):827-34.

Bilska, A., and L. Wlodek. 2005. Lipoic acid—the drug of the futrue? Pharmacol Rep 57: 570-577.

Bilska, A., M. Dubiel, M. Sokolowska-Jezewicz, E. Lorene-Koci, and L. Wlodek. Jun. 2007. Alpha-lipoic acid differently affects the reserpine-induced oxidative stess in the striatum and prefrontal cortex of rat brain. Neuroscience 146: 1758-1771.

Bitar, M. S., S. Wahid, C. W. Pilcher, E. Al-Saieh, and F. Al-Mulla. 2004. Alpha-lipoic acid mitigates insulin resistance in Goto-Kakizaki rats. Hormone and metabolic research. Hormon- and Stoffwechselforschung 36: 542-549.

Blanco, R. A., T. R. Ziegler, B. A. Carlso, P. Y. Cheng, Y. Park, G. A. Cotsouis, C. J. Accardi, D. P. Jones. Oct. 2007. Diurnal variation in glutahione and cysteine redox states in human plasma. The American journal of clinical nutrition 86: 1016-1023.

Blankenship, T. N., J. F, Hess, and P. G. FitzGerald. 2001. Development- and differentiation-dependent reorganization of intermediate filaments in fiber cells. Investigative ophthalmology & visual science 42: 735-742.

Bonomi, L et al. 1990. Evaluation of the 701 interzeag lens opacity meter. Graefe's Arch Clin Exp Ophthalmol 228(5):447-9.

Borja, D et al. Jun. 2008. Optical Power of the Isolated Human Crystalline Lens. Invest Ophthalmol Vis Sci 49(6):2541-8.

Bron, A.J., et al. "The Ageing Lens" Ophthalmologica (2000) 214(1):86-104.

Brunkener, M., and S. D. Georgatos. 1992. Membrane-binging properties of filensin, a cytoskeletal protein of the lens fiber cells. Journal of cell science 103 (Pt 3): 709-718.

Cenedella, R. J. 1998. Prenylation of proteins by the intact lens. Investigative ophthalmology & visual science 39: 1276-1280.

Croft, M. A., A. Glasser, G. Heatley, J. McDonald, T. Ebbert, N. V. Nadkarni, and P. L. Kaufman. 2006. The zonula, lens, and circumlental space in the normal iridecromized rhesus monkey eye. Investigative ophthalmolgy & visual science 47: 1087-1095.

Croft, M. A., and P. L. Kaufman. 2006. Accommodation and presbyopia: the ciliary neuromuscular view. Ophthalmology clinics of North America 19: 13-24.

Dubbelman, M., G. L. Van der Heijde, H. A. Weeber, and G. F. Vrensen. 2003. Changes in the internal structure of the human crystalline lens with age and accomodations. Vision research 43: 2363-2375.

Eason, R. C., H. E. Archer, S. Akhfar, and C. J. Bailey. 2002. Lipoic acid increases glucose uptake by skeletal muscles of obese-diabetic ob/ob mice. Diabetics Obes Metab 4:29-35.

Egan, D., P. James, D. Cooke, and R. O'Kennedy. 1997. Studies on the cystostatic and cytotoxic effects and mode of action of 8-nitro-7-hydroxycoumarin. Cancer letters 118: 201-211.

Finn, G., B. Creaven, and D. Egan. 2003. Modulation of mitogen-activated protein kinases by 6-nitro-7-hydroxycoumarin mediates apoptosis in renal carcinoma cells. European Journal of pharmacology 481: 159-167.

Finn, G. J., B. S. Creaven, and D. A. Egan. 2004. A study of the role of cell cycle events mediating the action of courmarin derivatives in human malignant melanoma cells: Cancer letters 214: 43-54.

Flammer J, Beble H. 1987. Lens Opacity Meter: a new instrument to quantify lens opacity. Ophthalmologica 195(2):69-72.

Furuta, T., S. S. Wang, J. L. Dantzker, T. M. Dove, W. J. Bybee, E. M. Callaway, W. Denk, and R. Y. Tsien. 1999. Brominated 7-hydroxycoumarin-4ylmethyls: photolabile protecting groups with biologically useful cross-sections for two photon photolysis, Pro-

(56) References Cited

OTHER PUBLICATIONS ceedings of the National Academey of Sciences of the United States of America 96: 1193-1200.
Gail MH & You WC. 2006. A factorial trial including garlic supplements assesses effect in reducing precancerous gatstric lesions. J Nutr. 136(3 Suppl):813S-815S.
Garner, M. H., and J. Horwitz. 1994. Catalytic subunit isoforms of mammalian lens Na,K-ATPase; Current eye research 13: 65-77.
Garner, M. H., and Y. Kong. 1999. Lens epithielium and fiber Na,K-ATPases: distribution and localization by immunocytochemistry. Investigasive ophthalmology & visual science 40: 2291-2298.
Garner, M. H., and J. R. Kuszak. 1993. Cations, oxidants, light as causative agents in senile cataracts. Puerto Rico health sciences journal 12: 115-122.
Garner, M. H., and A. Spector. 1980. Selective oxidation of cysteine and methlonine in normal and senile cataractous lenses. Proceedings of the National Academy of Sciences of the United States of America 77: 1274-1277.
Garner, M. H. 1994. Na,K-ATPases of the lens epithelium and fiber cell: formation of catalytic cycle intermediates and Na+: K+ exchange. Experimental eye research 58: 705-718.
Gilmore WJ & Kirby GM. 2004. Endoplasmic reticulum stress due to altered cellular redox status positively regulates murine hepatic CYP2A5 expression. J Pharmacol Exp Ther. 308(2):660-8. Epub Nov. 10, 2003.
Glasser, A., and M. C. Campbell. 1999. Biometric, optical and physical changes in the isolated human crystalline lens with age in relation to presbyopia. Vision research 39: 1991-2015.
Goulielmos, G., F. Gounari, S. Remington, S. Muller, M. Haner, U. Aebi, S. D. Georgatos. 1996. Filensin and phakinin form a novel type of beaded intermediate filaments and coassemble de novo in cultured cells. The Journal of cell biology 132: 643-655.
Goulielmos, G., S, Remington, F. Schwesinger, S. D. Georgatos, and F. Gounarl. 1996. Contributions of the structural domains of filensin in polymer formation and filament distribution. Journal of cell science 109 (Pt 2): 447-456.
Green DR & Reed JC. 1998. Mitochondria and apoptosis. Science 281(5381):1309-12.
Gruzma, A., A. Hidmi, J. Katzhendler, A. Haj-Yehie, and S. Sasson. 2004. Synthesis and characterization of new and potent alpha-lipoic acid derivatives. Bioorganic & medicinal chemistry 12: 1183-1190.
Guest, P. C., H. A. Skynner, K. Salün, F. D. Tattersall, M. R. Knowles, and J. R. Atack. 2006. Detection of gender differences in rat lens proteins using 2-D-DIGE. Proteomics 6: 667-676.
Gurney, AM. 1994. Flash photolysis of caged compounds in Microelectrode Techniques, ed Ogden D, pp. 389-406.
Halhal M, et al. 2004. Iontophoresis: from the lab to the bed side. Exp Eye Res 78(3):751-57.
Halleck MM, et al, 1997. Reduction of trans-4,S-dihydroxy-1,2-dithlane by cellular oxidoreductases activites gadd153/chop and grp7S transcription and induces cellular tolerance in kidney epithelial cells. J Biol Chem. 272(35):21760-6.
Hardie, R.C. 1995. Photolysis of Caged Ca2+ Facilitates and inactivates but does not Directly Excite Light-Sensitive Channels in *Drosophila* Photoreceptors. The Journal of Neuroscience 15(1):599-902.
Heidemann, S. R., S. Kaech, R. E. Buxbaum, and A. Matus. 1999. Direct observations of the mechanical behaviors of the cytoskeleton in living fibroblasts. The Journal of cell biology 145: 109-122.
Hermans, E., M. Dubbelman, R. van der Heijde, and R. Heethaar. Jul. 2007. The shape of the human lens nucleus with accommodation. Journal of vision 7: 16.1-10.
Hoenders, H.J., et al. "Lens proteins and aging" J Gerontol (May 1983) 38(3):278-86.
Holmann, M., P. Mainka, H. Tritschler, J. Fuchs, and G. Zimmer. 1995. Decrease of red cell membrane fluidity and -SH groups due to hyperglycemic conditions is counteracted by alpha-lipoic acid. Archives of biochemistry and biophysics 324: 85-92.
Hung CC, et al. 2003. Protection of renal epithelial cells against oxidative injury by endoplamic reticulum stress preconditioning is mediated by ERK 1/2 activation. J Biol Chem. 278(31):29317-26. Epub May 8, 2003.
Ivanov, D., G. Dvoriantchlkova A. Pestova, L. Nathanson, and V. I. Shestopalov. 2005. Microarray analysis of fiber cell mutation in the lens. FEBS letters 579: 1213-1219.
Janoria, K. G., S,. Hariharan, D. Paturi, D. Pal, and A. K. Mitra. 2006. Biotin uptake by rabbit corneal epithelial cells: role of sodium-dependent multivitamin transporter (SMVT). Current eye research 31: 797-809.
Jimenez-Orozco, F. A., J. S. Lopez-Gonzalez, A. Nieto-Rodriguez, M. A. Vainsco-Velazquez, J. A. Molina-Guarneros, N. Mendoza-Patino, M. J. Garcia-Mondragon, P. Elizalde-Galvan, P. Leon-Cedeno, and J. J. Mandoki. 2001. Decrease of cyclin D1 in the human lung adenocarcinoma cell line A-427 by 7-hydroxycoumarin. Lung cancer (Amsterdam, Netherlands) 34: 185-194.
Johansson, M., and M. Lundberg. Dec. 2007. Glutathionylation of beta-actin via a cysteinyl sulfenic acid interordinary. BMC Biochem 8: 26.
Jones, D. P., Y. M. Go, C. I., Anderson, T. R. Ziegler, J. M. Kinkade, Jr., and W. G. Kirlin. 2004. Cysteine/oystine couple is a newly recognized node in the circuitry for biologic redox signaling and control. Faseb J 18: 1246-1248.
Jung MY, et al. 2001. Chemopreventive allylthlopyridazine derivatives induce apoptosis in SK-Hep-1 hepatocarcinoma cells through a capase-3-dependant mechanism. Eur J Cancer. 37(16):2104-10.
Jürgen, W. Mar. 2007. Synthesis and investigations of (6-hydroxy-3-oxo-3H-xanthen-9-yl)methyl derivatives. A new photoremovable protecting group. Inaugural Dissertation at Universität Basel.
Kuhn, J., P. Preis, F. Waidman, and A. Tseng, Jr. 1994. Coumarin modulates the cell-cycle progression of an MTV-EJras cell line. Journal of cancer research and clinical oncology 120 Suppl: S19-22.
Kao, J.P.Y. 2006. Caged Molecules: Principles and Practical Considerations. Current Protocols in Neuroscience. 6.20.1-6.20.21.
Kibbelaar, M. A., F. C. Ramaekers, P. J. Ringens, A. M. Seiten-Versteegen, L. G. Poels, P. H. Jap, A. L. van Rossum, T. E. Feltkamp, and H. Bloemendal. 1980. Is actin in eye lens a possible factor in visual accomodation? Nature 285: 506-508.
Kim DH, et al. 2005. Aqueous penetration and biological activity of moxifloxacin 0.5% ophthalmic solution and gatifloxacin 0.3% solution in cataract surgery patients. Ophthalmology 112(11):1992-6. Epub Sep. 23, 2005.
Konrad, D., R. Somwar, G. Sweeney, K. Yaworsky, M. Hayashi, T. Ramlal, and A. Klip. 2001. The antihyperglycemic drug alpha-lipoic acid stimulates glucose uptake via both GLUT4 translocation and GLUT4 activation: potential role of p38 mitogen-activated protein kinase in GLUT4 activation. Diabetes 50: 1464-1471.
Krueger, R.R., et al. "Experimental increase in accommodative potential after neodymiam: yttrium-aluminum-garner laser photodisruption of paired cadaver lenses" Ophthalmology (2001) 108(11):2122-29. (Abstract only).
Krumdieck, C.L., et al. "Mechanism of Homocysteine Toxicity on Connective Tissues: Implications for the Morbidity of Aging" J. Nutr. (2000) 130:365S-68S.
Kumar RV, et al. 1991. The nature of inhibition of 3-hydroxy-3-methylglutaryl CoA reductase by garlic-derived diallyl disulfide. Biochim Biophys Acta. 1078(2):219-25.
Kuszak, J. R., A. R. Khan, and R. J. Cenedella. 1988. An ultrastructural analysis of plamsa membrane in the U18666A cataract. Investigative ophthalmology & visual science 29: 261-267.
Lacy, A., and R. O'Kennedy. 2004. Studies on coumarins and coumarin-related compounds to determine their therapeutic role in the treatment of cancer. Current pharmaceutical design 10: 3797-3811.
Larsson, H. P., A. V. Tzingounis, II. P. Koch, and M. P. Kavanaugh. 2004. Fluorometric measurements of conformational changes in glutamate transporters. Proceedings of the National Academy of Sciences of the United States of America 101: 3951-3956.
Lee V & Bundgaard H. 1992. Improved Ocular Drug Delivery with Prodrugs, In: Sloan K. ed. Prodrugs: Topical and Ocular Drug Delivery, vol. 53, p. 233.

(56) References Cited

OTHER PUBLICATIONS

Lesinski L. & Duschmale J. 2006. Flash Pholoysis in Pralaikum "Physikalisehe Chemie" pp. 1-8.

Li, L. J. Lim, M. D. Jacobs, J. Kistler, and P. J. Donaldson. Mar. 2007. Regional differences in oystine accumilation point to a suteral delivery pathway to the lens core. Investigative ophthalmology & visual science 48: 1253-1260.

Lim, J., Y. C. Lam, J. Kistler, and P. J. Donaldson. 2005. Molecular characterization of the cystine/glutamate exchanger and the excitatory amino acid transporters in the rat lens. Investigative ophthalmology & visual science 46: 2869-2877.

Lim, J., L. Li, M. D. Jacobs, J. Kistler, and P. J. Donaldson. Nov. 2007. Mapping of glutathione and its precursor amino acids reveals a role for GLYT2 in glycine uptake in the lens core. Investigative ophthamology & visual science 48: 5142-5151.

Lindsey Rose, K. M., R. G. Gourdic, A. R. Presced, R. A. Quinlan, R. K. Crouch, and K. L., Schey. 2006. The C terminus of lens aquaporin 0 interacts with the cytoskeletal proteins filesin and CP49. Investigative ophthalmology & visual science 47: 1562-1570.

Liu H, et al. 1997. Endoplasmic reticulum chaperones GRP78 and calreticolin prevent oxidative stress, Ca2+ disturbances, and cell death in renal epithelial cells. J Biol Chem. 272(35):21751-9.

Liu, J., E. Head, A. M. Gharib, W. Yuan, R. T. Ingersoll, T. M. Hagen, C. W. Cotman, and B. N. Arnes. 2002. Memory loss in old rats is associated with brain mitochondrial decay and RNA/DNA oxidation: partial reversal by feeding acetyl-L-carnitine and/or R-alpha -lipoic acid. Proceedings of the National Academy of Sciences of the United States of America 99:2356-2361.

Lopez-Gonzalez, J. S., H. Prado-Garcia, D. Aguilar-Cazares, J. A. Molina-Guarnerus, J. Morales-Fuentes, and J. J. Mandoki. 2004. Apoptosis and cell cycle disturbances induced by coumrain and 7-hydroxycoumarin on human lung carcinoma cell lines. Lung cancer (Amsterdam, Netherlands) 43:275-283.

Luo, S., V. S. Kansara, X. Zhu, N. K. Mandava, D. Pal, and A. K. Mitra. 2006. Functional characterization of sodium-dependent multivitamin transporter in MDCK-MDRI cells and its utiliztion as a target for drug delivery. Mol Pharm 3:329-339.

Maitra, J., E. Serbinova, H. J. Tritschler, and L. Packer. 1996. Stereospecific effects of R-lipoic acid on buthionine sulfoximine-induced cataract formation in newborn rats. Biochemical and biophysical research communications 221: 422-429.

Maitra, I., E. Serbinova, H. Trischler, and L. Packer. 1995. Alpha-Tipoic acid prevents buthionine sulfoximine-induced cataract formation in newborn rats. Free radical biology & medicine 18: 823-829.

Manns, F., J. M. Parel, D. Denham, C. Billotte, N. Ziebarth, D. Borja, V. Fernandez, M. Aly, E. Arrietu, A. Ho, and B. Holden. Jul. 2007. Optomechanical response of human and monkey lenses in a lens stretcher. Investigative ophthalmology & visual science 48: 3260-3268.

Merdes, A., M. Brunkener, H. Horstmann, and S. D. Georgatos. 1991. Filesin: a new yimentin-binding, polymerization-competent, and membrane-associated protein of the lens fiber cell. The Journal of cell biology 115: 397-410.

Merdes, A., F. Gountari, and S. D. Georgatos. 1993. The 47-kD lens-specific protein phakinin is a tailess intermediate filament protein and an assembly partner of filensin. The Journal of cell biology 123: 1507-1516.

Moffat, B.A., et al. "Age-related Changes in the Kinetics of Water Transport in Normal Human Lenses" Exp. Eye Res. (1990) 69(6):663-69.

Moini, H., O. Tirosh, Y. C. Park, K. J. Cho, and L. Packer. 2002. R-alpha-lipoic acid action on cell redox status, the insulin receptor, and glucose uptake in ST3-L1 adipocytes. Archives of biochemistry and biophysics 397: 384-391.

Muchowski, P. J., M. M. Valdez, and J. I. Clark. 1999. AlphaB-crystallin selectively targets intermediate filament proteins during thermal stress. Investigative ophthalmology & visual science 40: 951-958.

Mask SR, et al. 1997. Cytotoxicity and genotoxicity of diallyl sulfide and diallyl disulfide towards Chinese hamster ovary cells. Food Chem Toxicol. 35(3-4):379-85.

Newell. 1996. Ophthalmology: Principles and Concepts St. Louis: Mosby-Year Book St. Louis, p. 83.

Obrosova I, et al. 1998. Diabetes-induced changes in lens antioxidant status, glucose utilization and energy metabolism: effect of DL-alpha-lipoic acid. Diabetologia. 41(12):1442-50.

Ong, M. D., D. M. Payne, and M. H. Garner. 2003. Differential protein expression in lens epithelial whole-mounts and lens epithelial cell cultures. Experimental eye research 77: 35-49.

Pau, H., and J. Kranz. 1991. The increasing sclerosis of the human lens with age and its relevance to accommodation and presbyopia. Graefe's archived for clinical and experimental ophthalmology—Albrecht von Graefes Archiv fur klinische und experimentelle Ophthalmologie 229: 294-296.

Petit PX, et al. 1995. Alterations in mitochondrial structure and function are early events of dexamethasone-induced thymocyte apoptosis. J Cell Biol. 130(1):157-67.

Phelps-Brown, N.A., et al. "Nutritional supplements and the eye" Eye (1998) 12:127-33.

Pierscionek, B. K. 1995. Age-related response of human lenses to stretching forces. Experimental eye research 60: 325-332.

Reddy, N. S., K. Gumireddy, M. R. Mallireddigari, S. C. Cosenza, P. Venkatapuram, S. C. Bell, E. P. Reddy, and M. V. Reddy. 2005. Novel coumarin-3-(N-aryl)carboxamides arrest breast carrier cell growth by inhilating ErbB-2 and ERK1. Bioorganic & medicinal chemistry 13: 3141-3417.

Salvioli S, et al. 1992. JC-1, but not DiOC6(3) or rhodamine 123, is a reliable fluorascent probe to assess delta psi changes in intact cells: implications for studies on mitochondrial functionality during apoptosis. FEBS Lett. 411(1):77-82.

Sandilands, A., A. R. Prescott, A. M. Hutcheson, R. A. Quinlan, J. T. Casselman, and P. G. FitzGerald. 1995. Filensin is proteolytically processed during tests fiber cell differentation by multiple independent pathways. European journal of cell biology 67: 238-253.

Serraf D & Lee DA. 1994. The Role of Ioatophoresis in Ocular Drug Delivery. J Ocul Pharmacol 10(1):69-81.

Sato, H., M. Tamba, K. Kuriyama-Matsumura, S. Okuno, and S. Bannai. 2000. Molecular cloning and expression of human nCT, the light chain of amino acid transport system xc. Antioxid Redox Signal 2: 665-671.

Sato, H., M. Tamba, T. Ishii, and S. Bannai. 1990. Cloning and expression of a plasma membrane cystine/glutamate exchange transporter composed of two distinct proteins. The Journal of biological chemistry 274: 11455-11458.

Sato, H., A. Shiiya, M. Kimata, K. Maebara, M. Tamba, Y. Sakakura, N. Makino, F. Sugiyama, K. Yagami, T. Moriguchi, S. Takahashi, and S. Bannai. 2005. Redox imbalance in cystin/gluamate transporter-deficient mice. The Journal of biological chemistry 280: 37423-37429.

Schonheit, K., L. Gille, and H. Nohl. 1995. Effect of alpha-lipoic acid and dihydrolipoic acid on ischemia-reperfusion injury of the heart and heart mitochondria. Biochimica et biophysics acts 1271: 335-342.

Senda, N. 2006. Synthesis and Photochemical Properties of a New Water-Soluble Coumarin, Designed as a Chromophore for Highly Water-Soluble and Photolabile Protecting Group. Bull. Chem. Soc. Jpn. vol. 79, No. 11, 1753-1757.

Shembekar, V. R., Y. Chen, B. K, Carpanter, and G. P. Hess. 2005. A protecting group for carboxylic acids that can be photolyzed by visible light. Biochemistry 44: 7107-7114.

Spector, A., et al. "Thioredoxin fragment 31-36 is reduced by dihydrolipoamide and reduces oxidized protein" Biochem Biophys Res Commun (Jan. 1988) 150(1):156-62.

Strenk, S. A., L. M. Strenk, J. L. Semmiow, and J. K. DeMarco. 2004. Magnetic resonance imaging study of the effect of age and accommodation on the human lens cross-sectional area. Investigative ophthalmology & visual science 45: 539-545.

Sundaram SG & Milner JA. 1996. Diallyl disulfide soppresses the growth of human colon tumor cell xenografts in athymic nude mice. J Nutr. 126(5):1355-61.

(56) References Cited

OTHER PUBLICATIONS

Sweeney, M. H., and R. J. Truscott. 1998. An impediment to glutebione diffusion in older normal human lenses: a possible precondition for nuclear cataract. Experimental eye research 67: 587-595.
Tamm, E., E. Lntjen-Drecoll, W. Jungkunz, and J. W. Rohen. 1991. Posterior attachment of ciliary muscle in young, accommodationg old, presbyopic monkeys. Investigative ophthalmology & visual science 32: 1678-1692.
Tamm, S., E. Tamm, and J. W. Rohen. 1992. Age-related changes of the human ciliary muscle. A quantative morphometric study. Mechanisms of ageing and development 62:209-221.
Truscott, R. J. 2000. Age-related nuclear cataracts: a lens transpot problem. Ophthalmic research 32: 185-194.
Wang, C. J., V. J. Hsieh, C. Y. Chu, Y. L. Lin, and T. H. Tseng. 2002. Inhibition of cell cycle progression in human leukemia 11L-60 cells by escaletin. Cancer Letters 183: 163-168.
Wang, S. J., and H. H. Chen. Jan. 2007. Presynaptic mechanisms underlying the alpha-lipoic acid facilitaition of glutamate exocytosis in rat cerebral cortex nerve terminals. Neurochemistry international 50: 51-60.
Weeber, HA et al. Feb. 2007. Stiffness gradient in the crystalline lens. Graefes Arch Clin Exp Ophthalmol 245(9):1357-66.
Widomska, J., M. Raguz, J. Dillon, E. R. Gaillard, and W. K. Subczynski. Jun. 2007. Physical properties of the lipid bilayer memebrane made of cell lens lipids: EPR spin labeling studies. Biochimica et biophysica acia 1768: 1454-1465.
Wieboldt, R. et al. 1994. Photolabife precursors of glutamate: Synthesis, photochemical properties, and activation of glutamate receptors on a microsecond time scale. Proc. Natl. Acad. Sci. 91:8752-8756.
Willner I & Zahavy E. 1994. Activation of Glutathione Reducase by Light: A Novel Approach to Design Redox Photo-Enzymes. Agnew Chem Int Ed Engl 33(5):581-83.
Yin MC, et al. 2002. Nonenzymatic antioxidant activity of four organosulfur compounds derived from garlic. J Agric Food Chem. 50(21):6143-7.
Yu, N. T., D. C. DeNagel, P. L. Pruett, and J. F. Kuck, Jr. 1985. Disolfide bond formation in the eye lens. Proceedings of the National Academy of Sciences of the United States of America 82: 7965-7968.
Zhao, Y., Q. Zheng, K. Dakin, K. Xu, M. L. Martinez, and W. H. Li. 2004. New caged coumarin fluorophores with extaordinary uncaging cross sections suitable for biological imaging applications. Journal of the American Chemical Society 126: 4653-4663.
Zivkovic, D. Apr. 2007. Investigation 2,7-diamine-9-flaorepol photochemistry. Inaugural Dissertation at Universitat Basel.
Ip C. Ganther HE. 1992. Comparison of solenium and sulfur analogs in cancer prevention. Carcinogenesis. 13(7): 1167-70.
Bustamante, J., et al., 1998. α-Lipoic Acid in Liver Metabolism and Disease. Free Radical Biology & Medicine 24: No. 6 1023-1039.
Cagini, C. MD, et al. 2010. Study of alpha-lipoic noid penetration in the human aqueous humour after topical administration. Clinical and Experimental Ophthalmology "Accepted Article" doi: 10.1111/j. 1142-9071.2010.02319.x.
Giblin FJ, et al. 1979. The effects of X-irradiation on lens reducing systems. Investigative Ophthalmology & Visual Science 18:468-475.
Kramár P, et al. 1987. Thermal cataract formation in rabbits. NCBI Pubmed abstract, PMID: 3426637, abstract Bioelectromagnetics 8:397-406. (Abstract only).
Li, X., Liu, Z., et al. Apr. 2008. Lipoamide protects retinal pigment epithelial cells from oxidative stress and mitochondrial dystinction. Free Radic Biol Med. 44(7): 1465-1474.
Lipman RM, et al. 1988. Cataracts induced by Microwave and Ionizing Radiation. NCBI Pubmed abstract, PMID: 3068822, abstract of Snrv. Ophtalmol 33:200-210, (Abstract only).
Trayburn P. and Van Heyningen R. 1973. The Metablolism of Amino Acids in the Bovine Lens: Their Oxidation as a Source of Energy. Biochem. J. 136:67-75.
Wakabayashi, Y. et al. 2006. Glutamate Levels in Aqueous Humor of Patients with Retinal Artery Occlusion. Retina 26:432-436.
Zwingmann, C. et al. 2001. 13C Isotopmer Analysis of Glucose and Alanine Metabolism Reveals Cytosolic Pyruvate Compartmentation as Part of Energy Metabolism in Astrocytes. GLIA 34:200-212.
Aloisi et al. 1948. Glycerylphophyoryletholine and Choline Glycerophosphate. Biochemical Journal. vol. 43, pp. 154-161; p. 157, col. 1, para 2-3; col. 2, para 1; p. 158, col. I, para 4.
Gilbert, Basic Concepts in Biochemistry USA. McGraw Hill 2000 p. 184.
Jablonski et al. Plant Physilogy 1978 61:221-225.
Ng et al. Experimental Eye Research 1986 43:477-489.
Morris Jr. Recent advances in arginine metabolism; roles and regulation of the arginases. British Journal of Pharmacology, E-Pub Jun. 5, 2009, 157(6):922-930.
PubChem Compound Summary CID 863 lipoamide (Sep. 16, 2004) (Retrieved from the internet Nov. 13, 2010; http://pubchem.ncbi.nlm.nih.gov/summary/summary;cgi?cid=863).
Salceda, et al. L-arginine uptake in normal and diabetic rat, retina and retinal pigment spithelhim. Neurochem Res., Aug. 2008, 33(8):1541-1545.
Stuehr et al. Nw-Hydroxy-L-arginine is an intermediate in the Biosynthesis of nitric Oxide from L-Arginine. The Journal of Biological Chemistry 1991, 266(10):6259-6265.
Truscott, Presbyopia. Emerging from a blur towards and understanding of the molecular basis for the most common eye condition. Exp Eye Res., Epub Jul. 2008, 88(2):241-247; p. 241, col. 1; p. 242, col. 1; p. 245, col. 1.
Glasser, A., "Restoration of accommodation: surgical options for correction of presbyopia," *Clin Exp Optom* 91(3):279-295, Australian Optometrists Association, Australia (May 2008).
McGinty, S. J., and Truscott, R. J. W., "Presbyopia: the first stage of nuclear cataract?" *Opthalmic Res* 38(3):137-148, Karger, Switzerland (Jan. 2006).
Michael, R., and Bron, A. J., "The ageing lens and cataract: a model of normal and pathological ageing," *Phil, Trans. R. Soc. B* 366(1568):1278-1292, The Royal Society, England (Mar. 2011).
Truscott, R J. W., and Zhu, X., "Presbyopia and cataract: a question of heat and time," *Prog Retin Eye Res* 29(6):487-499, Elsevier Ltd., England (Nov. 2010).
Aunaca, Galízar, "Antioxidant Effects of Sulfur-Containing Amino Acids," Yonsei Medical Journal 45(5): 776-788. Yonsei University, Korea (2004).
Draize J., et al., "Methods for the Study of Irritation and Toxicity of Substances Applied Topically to the Skin and Mucous Membranes," Journal of Pharmacology and Experimental Therapeutics 82:377-390. American Society for Pharmacology and Experimental Therapeutics. United States (1944).
International Search Report and Written Opinion for International Application No. PCT/US2015/018505, International Search Authority, United States, dated May 27, 2015, 10 pages.
Zhang, Ruhua, Industrial Pharmacy, China Medical Science and Technology Press. Jul. 2011, 1st edition, pp. 55, 59.
English Language Translation of Notification of Reexamination dated Sep. 22, 2020 for Chinese Patent Application No. 201580012000.6 (10 pages).
Remington, The Science and Practice of Pharmacy, Nineteenth Edition 1995, pp. 1463, 1556-1547.

EYE DROP PENETRATION

| Treatment | LA | BIOPTIN | |
|---|---|---|---|
| TEST GROUP | Percent Penetration | | ENHANCEMENT FACTOR |
| RABBIT | 3.0% | 17.8% | 6.0 |
| MOUSE | 3.0% | 16.2% | 5.92 |
| HUMAN | 0.37% (1) | 2.2% Estimated | 5.96 |

REFERENCES
(1) Carlo Cagini et al "Study of alpha-lipoic acid penetration in the human aqueous humour after topical administration" Clinical and Experimental Ophthalmology, 38; Lipoic acid (LA)

Fig. 3

LIPOIC ACID CHOLINE ESTER COMPOSITIONS AND METHODS OF USE

This application is a continuation of U.S. application Ser. No. 15/118,910 filed 15 Aug. 2016, now abandoned, which is U.S. National Phase filing of International Application No. PCT/US2015/018505 filed 3 Mar. 2015, which claims priority to U.S. Application No. 61/947,378 filed 3 Mar. 2014, the contents of which are incorporated herein by reference in their entirety.

FIELD OF THE INVENTION

The present invention generally relates to pharmaceutical compositions comprising lipoic acid choline ester or derivatives thereof and anon-aqueous excipient and uses thereof for treating ocular diseases or disorders (e.g., presbyopia).

BACKGROUND OF THE INVENTION

Presbyopia and Accommodative Amplitude

As we age, our lenses undergo physiological changes that make it more difficult to focus on near objects. That is why nearly everyone requires reading glasses, even as early as ages 35-40. The ability of the eye to change focal power, also known as accommodative amplitude, decreases significantly with age. The accommodative amplitude is 20 diopters in children and young adults, but it decreases to 10 diopters by age 25 and to 1 diopter by age 60. The age-related inability to focus on near objects is called presbyopia. All of us will develop presbyopia and will use corrective lenses unless a new treatment is found.

Many factors contribute to the cause of presbyopia. A lens fiber cell fluid layer formed during accommodation by aquaporin-0 (see FIG. 1) has been implicated in presbyopia. As the diagram shows, when the ciliary muscle contracts (Helmholtz theory of accommodation), tension on the zonules is released and the potential energy stored in the lens capsule is released and creates kinetic force at the equatorial plane of the lens. As shown by finite element analysis of the lens, this force originates adjacent to the zonular lens attachments at the perilenticular equatorial position. The lens is made-up of long fiber cells with "new" cells made at the surface. These fiber cells form a microfluidic path that resemble "tubes." This works to maintain lens accommodative function. Dysfunctional "old" fiber cells are displaced inward. This provides an efficient means to move outer "fluid compartment" fluid, when zonular tension is released, toward the middle (central optical axis) of the lens to increase geometric curvature (optical power). This fluid movement is facilitated by a special phenomena similar to that reported for blood flow through microcapillaries (<10 um). A small plasma layer (a phenomenon described by Fahraeus-Lindqvist) is formed along the periphery of blood vessels. This lowers the apparent or effective measured hematocrit viscosity and improves blood flow with lower backpressure.

Within lens fiber cells (also about 10 um diameter), a similar phenomenon is apparently operational. Abundant aquaporin-O lining the cell wall/membrane in lens fiber cells allows water flow out of the cell during accommodation for near vision focus. Dissolved micronutrients (including, therapeutic pharmaceuticals) are supplied to the lens occur through these same interstitial water channels. Additionally, part of their undocumented intrinsic function facilitates accommodative amplitude that requires aforementioned fluid movement to change lens geometry. The water layer formed along the intracellular fiber cell membrane wall reduces impedence or resistance and gives "lubrication" to the inner core cytosol protein; a previously overlooked phenomena. Although the protein core (inside the inner portion of the lens fiber cell) may have higher intrinsic viscosity, the "lubrication factor" or microlayer (<1 nm) formed between the core and the inner membrane, significantly lowers the extrinsic viscosity (as with blood hematocrit apparent viscosity). This allows the lens cytosol to move forward to the central visual axis within confines of limited zonular force to increase optical power.

Loss of this water layer means that a greater force is required to move the fluid from the equatorial to optical path (for increased geometric curvature-optical power). Similarly, when aquaporin-0 structure-function is compromised by disulfide bond formation to the core protein as a result of oxidative stress with age, this function layer is compromised and rendered inoperative.

BRIEF SUMMARY OF THE INVENTION

The inventors have found that lipoic acid choline ester ("LACE") (see e.g., U.S. Pat. No. 8,410,462) can restore this critical fluid layer responsible for fluid movement, restore near vision, and reduce the core lens cytosol modulus that is affected by disulfide cross-linking. Thus, LACE formulations are in need for treating ocular diseases or disorders (e.g., presbyopia) where the critical fluid layer is lost or where disulfide cross-linking is an issue.

In various embodiments, the invention provides a pharmaceutical composition comprising a therapeutically effective amount of lipoic acid choline ester or derivatives thereof and a non-aqueous excipient. In some embodiments, the therapeutically effective amount of lipoic acid choline ester and the non-aqueous excipient are mixed in an aqueous solution having a pH of 4 to 8 (e.g., 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, or any ranges based on these specified numeric values). In some embodiments, the aqueous solution comprises a buffer agent. In some embodiments, the pharmaceutical composition is free of a buffer agent.

In some embodiments, the pharmaceutical composition comprises a therapeutically effective amount of lipoic acid choline ester and a non-aqueous excipient, mixed in an aqueous solution having a pH of 4 to 6, wherein at least 95% of the lipoic acid choline ester is present in the pharmaceutical composition, as measured by HPLC, following storage at 25° C. under 40% relative humidity for 3 months. In some embodiments, the pharmaceutical composition is characterized in that less than 2% of the lipoic acid choline ester in the composition is degraded following storage at 25° C. under 40% relative humidity for 3 months. In some embodiments, the pharmaceutical composition is characterized in that the pharmaceutical composition has less than 12% total drug related impurities based on area-under-the-curve as determined by HPLC following storage at 25° C. under 40% relative humidity for 3 months. In some embodiments, the pharmaceutical composition is characterized in that the pharmaceutical composition has less than 7% of a drug related impurity based on area-under-the-curve as determined by HPLC following storage at 25° C. under 40% relative humidity for 3 months, wherein the drug related impurity is characterized by a relative retention time of 1.12 to 1.14. In some embodiments, the pharmaceutical composition is characterized in that the pharmaceutical composition has 4% of a drug related impurity based on area-under-the-curve as determined by HPLC following storage at 25°

C. under 40% relative humidity for 3 months, wherein the drug related impurity is characterized by a relative retention time of 0.65 to 0.66.

In some embodiments, the pharmaceutical composition is characterized by one or more of the following:
(a) having a concentration of the lipoic acid choline ester of 1% to 10% by weight of the composition;
(b) having a concentration of a preservative of 0.005% to 0.1% by weight of the composition;
(c) having a biochemical energy source of 0.1% to 5% by weight of the composition; and
(d) having a concentration of glycerol of 0.5% to 5% by weight of the composition. In some embodiments, the preservative is benzalkonium chloride and the biochemical energy source is alanine. In some embodiments, the lipoic acid choline ester has a counter ion selected from the group consisting of chloride, bromide, iodide, sulfate, methanesulfonate, nitrate, maleate, acetate, citrate, fumarate, hydrogen fumarate, tartrate (e.g., (+)-tartrate, (−)-tartrate, or a mixture thereof), succinate, benzoate, and anions of an amino acid such as glutamic acid.

In some embodiments, the pharmaceutical composition is prepared by mixing the therapeutically effective amount of lipoic acid choline ester and the non-aqueous excipient sequentially or simultaneously with the aqueous solution. In some embodiments, the pharmaceutical composition is prepared by first mixing the therapeutically effective amount of lipoic acid choline ester and the non-aqueous excipient to form a non-aqueous composition, and then mixing the non-aqueous composition with the aqueous solution. In some embodiments, the non-aqueous composition can be a solution, an emulsion, or a suspension formed by mixing lipoic acid choline ester and the non-aqueous excipient. The mixing can be conducted under heat for a sustained period of time. The pharmaceutical composition prepared by either method can have a shelf-stability of at least 3 months (e.g., 3 months, 6 months, 9 months, 1 year, or more than 1 year).

In some embodiments, the invention provides a non-aqueous composition comprising lipoic acid choline ester or derivatives thereof and a non-aqueous excipient. In some embodiments, the non-aqueous excipient is substantially miscible with water. In some embodiments, the non-aqueous excipient is a non-hydrolytic solvent. In some embodiments, the non-aqueous excipient is an alcohol. In some embodiments, the alcohol is a polyol, e.g., glycerol or propylene glycol. In some embodiments, the non-aqueous excipient is a semifluorinated alkane.

In some embodiments, the non-aqueous composition comprises a non-aqueous solution obtained by mixing lipoic acid choline ester with the non-aqueous excipient. In some embodiments, the mixing is conducted at a temperature of 20° C. to 100° C. In some embodiments, the mixing is conducted at a temperature of 37° C. to 80° C.

In some embodiments, the concentration of lipoic acid choline ester or derivatives thereof in the non-aqueous composition is in a range of 0.1% to 40% by weight. In some embodiments, the lipoic acid choline ester has a counter ion selected from the group consisting of chloride, bromide, iodide, sulfate, methanesulfonate, nitrate, maleate, acetate, citrate, fumarate, hydrogen fumarate, tartrate (e.g., (+)-tartrate, (−)-tartrate, or a mixture thereof), succinate, benzoate, and anions of an amino acid such as glutamic acid.

In some embodiments, the invention provides an ophthalmic formulation comprising the non-aqueous composition mixed in an aqueous solution. In some embodiments, the aqueous solution comprises a buffer. In some embodiments, the ophthalmic formulation has a pH of 4 to 8. In some embodiments, the ophthalmic formulation has a pH of 4.5. In some embodiments, the ophthalmic formulation comprises at least one ingredient selected from the group consisting of a biochemically acceptable energy source, a preservative, a buffer agent, a tonicity agent, a surfactant, a viscosity modifying agent, and an antioxidant. In some embodiments, the non-aqueous composition is sterilized before mixing in the aqueous solution. In some embodiments, the aqueous solution is a sterilized solution.

In some embodiments, the ophthalmic formulation is characterized by one or more of:
(a) having a concentration of the lipoic acid choline ester or derivatives thereof from 1% to 10% by weight of the formulation;
(b) having a concentration of a preservative 0.005% to 0.1% by weight of the formulation;
(c) having a pH of 4 to 6;
(d) having a biochemical energy source of 0.1% to 5% by weight of the formulation;
(e) having a concentration of glycerol of 0.5% to 5% by weight of the formulation; and
(f) having a shelf-life stability of greater than 3 months. In some embodiments, the preservative is benzalkonium chloride and the biochemical energy source is alanine.

In some embodiments, the invention also provides a system or method of long-term storage of the pharmaceutical composition by storing the non-aqueous composition separately from the aqueous solution, for example, in a two-part device (e.g., as described herein) or in a kit. The separately stored non-aqueous composition can then be mixed with the aqueous solution prior to use.

In some embodiments, the system comprises a first compartment, a second compartment, and a seal separating the first and second compartments, wherein the first compartment comprises a non-aqueous composition of an active ingredient and a non-aqueous excipient, the second compartment comprises an aqueous solution, and wherein the system is activated upon breaking the seal and mixing the non-aqueous solution with the aqueous solution. In some embodiments, the active ingredient is lipoic acid choline ester or derivatives thereof and the non-aqueous excipient is an ophthalmically acceptable excipient. In some embodiments, the aqueous solution comprises a buffer. In some embodiments, both the non-aqueous composition and the aqueous solution are sterilized. In some embodiments, the active ingredient in the system has a shelf-stability of more than 3 months. In some embodiments, the active ingredient in the system has a shelf-stability of more than 6 months. In some embodiments, the active ingredient in the system after activation has a shelf-stability of more than 3 months.

In some embodiments, the invention provides a method of storing an active ingredient that is susceptible to hydrolysis in an aqueous solution, the method comprising (a) providing the active ingredient in a first compartment; (b) providing the aqueous solution in a second compartment; and (c) separating the first and second compartments with a seal, wherein the active ingredient in the first compartment is not in contact with the aqueous solution until just prior to usage by breaking the seal. In some embodiments, the active ingredient in the first compartment is a lyophilized powder or mixed with a non-hydrolytic solvent. In some embodiments, the active ingredient is lipoic acid choline ester or derivatives thereof, or a peptide.

In some embodiments, the invention also provides a method of treating or preventing presbyopia in a subject in need thereof, the method comprising administering to a lens or an eye of the subject an effective amount of any of the pharmaceutical composition described herein.

BRIEF DESCRIPTION OF THE DRAWINGS/FIGURES

FIG. 3 shows a comparison of delivering of lipoic acid following administration of a lipoic acid formulation and a lipoic acid choline ester formulation.

DETAILED DESCRIPTION OF THE INVENTION

Definitions

Figure 1:
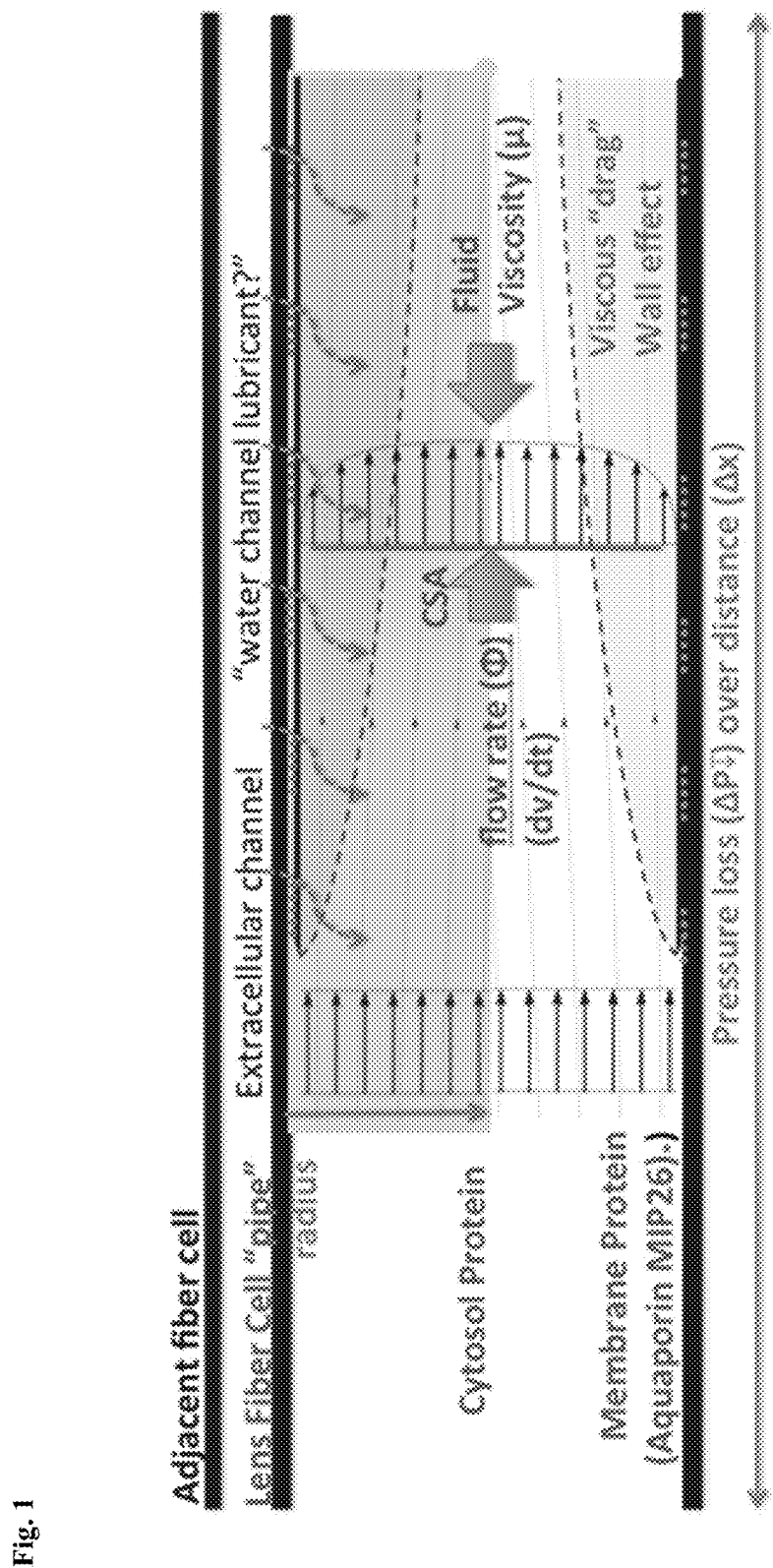
FIG. 1 shows the formation of a lens fiber cell fluid layer during accommodation by aquaporin-0.

Unless specifically stated or obvious from context, as used herein, the numeric values disclosed herein are understood as within a range of normal tolerance in the art, for example, within 10% of the stated value.

As used herein, the term "EV06," "LACE" or "lipoic acid choline ester" is understood to have the following chemical structure:

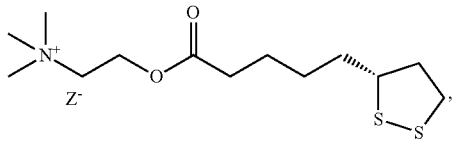 [SMILES: C[N+](C)(C)CCOC(=O)CCCC[C@@H]1CCSS1]

an optical isomer, or a mixture thereof. The counter ion (i.e., $Z^-$) of LACE can be any pharmaceutically acceptable anions. Non-limiting examples of counter ions include chloride, bromide, iodide, sulfate, methanesulfonate, nitrate, maleate, acetate, citrate, fumarate, hydrogen fumarate, tartrate (e.g., (+)-tartrate, (−)-tartrate, or a mixture thereof), succinate, benzoate, and anions of an amino acid such as glutamic acid. In some embodiments, the counter ion is chloride. In some embodiments, the counter ion is tartrate.

As used herein, "DIOPTIN™" formulations refer to lipoic acid choline ester formulations. For example, DIOPTIN™ 3% formulation refers to a formulation having 3% lipoic acid choline ester by weight of the formulation.

As used herein, a "derivative" of lipoic acid choline ester is understood as any compound or a mixture of compounds, excluding lipoic acid and choline, formed from reacting lipoic acid choline ester with a non-aqueous pharmaceutical excipient. In some embodiments, the derivative is a product formed from reacting lipoic acid choline ester with propylene glycol. In some embodiments, the derivative is a product formed from reacting lipoic acid choline ester with glycerol.

Unless specifically stated or obvious from context, as used herein, the term "excipient" refers to pharmaceutically acceptable excipient.

Open terms such as "include," "including," "contain," "containing" and the like mean "comprising."

The term "treating" refers to administering a therapy in an amount, manner, or mode effective to improve a condition, symptom, or parameter associated with a disease or disorder.

The term "preventing" refers to precluding a patient from getting a disorder, causing a patient to remain free of a disorder for a longer period of time, or halting the progression of a disorder, to either a statistically significant degree or to a degree detectable to one skilled in the art.

The term "therapeutically effective amount" refers to that amount of an active ingredient (e.g., LACE or derivatives thereof), which results in prevention or delay of onset or amelioration of symptoms of an ocular disease or disorder (e.g., presbyopia) in a subject or an attainment of a desired biological outcome, such as improved accommodative amplitude or another suitable parameter indicating disease state. Methods for determining the therapeutically effective amount for ocular applications are known, for example, as described in U.S. Pat. No. 8,410,162, the content of which is herein incorporated by reference in its entirety. For example, the therapeutically effective amount for treating or preventing presbyopia can be determined by measuring clinical outcomes including, but not limited to, the elasticity, stiffness, viscosity, density, or opacity of a lens.

As used herein, the term "shelf-stability" or "shelf stable" is understood as a character of or to characterize a composition or an active ingredient (e.g., LACE or derivatives thereof) that is substantially unchanged upon storing at 25° C. under 40% relative humidity (RH) for a period of time (e.g., 3 months). Methods for determining such shelf-stability are known, for example, shelf-stability can be measured by HPLC to determine the percentage of the composition or active ingredient (e.g., lipoic acid choline ester) that remains or has been degraded in a formulation following storing the formulation for a certain period of time. For example, shelf stable pharmaceutical composition can refer to a composition, which after being stored at 25° C. under 40% RH for 3 months, has at least 90% (e.g., 91%, 92%, 93%, 94%, 95%, 96%, 97%, 98%, 99%, or greater than 99%) of the active ingredient (e.g., lipoic acid choline ester) present in the composition as measured by HPLC. Shelf stable pharmaceutical composition can also refer to a composition, which after being stored at 25° C. under 40% RH for 3 months, has 5% or less (e.g., less than 4%, less than 3%, less than 2%, less than 1%, or less than 0.5%) of the active ingredient (e.g., lipoic acid choline ester) being degraded as measured by HPLC.

As used herein, the term "relative retention time" or "RRT" of a compound can be calculated using the equation "RRT=$(t_2-t_0)/(t_1-t_0)$," wherein $t_0$=void time, $t_1$=retention time of lipoic acid choline ester, and $t_2$=retention time of the compound.

The term "subject" as used herein generally refers to an animal (e.g., a pet) or human, including healthy human or a patient with certain diseases or disorders (e.g., presbyopia).

LACE Formulations

In various embodiments, the invention provides a pharmaceutical composition comprising a therapeutically effective amount of lipoic acid choline ester or derivatives thereof. In some embodiments, the pharmaceutical composition comprises a lyophilized powder comprising a therapeutically effective amount of lipoic acid choline ester or derivatives thereof. In some embodiments, the lyophilized powder also includes a non-aqueous excipient. In some embodiments, the lyophilized powder is obtained by lyophilizing any of the pharmaceutical compositions described herein.

In some embodiments, the pharmaceutical composition comprises a therapeutically effective amount of lipoic acid choline ester or derivatives thereof and a non-aqueous excipient. In some embodiments, the therapeutically effective amount of lipoic acid choline ester and the non-aqueous excipient are mixed in an aqueous solution having a pH of 4 to 8 (e.g., 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, or any ranges based on these specified numeric values). In some embodiments, the aqueous solution comprises a buffer agent. In some embodiments, the pharmaceutical composition is free of a buffer agent. In some embodiments, the aqueous solution is substantially oxygen free.

In some embodiments, the pharmaceutical composition is prepared by mixing the therapeutically effective amount of lipoic acid choline ester and the non-aqueous excipient sequentially or simultaneously with the aqueous solution. In some embodiments, the pharmaceutical composition is prepared by first mixing the therapeutically effective amount of lipoic acid choline ester and the non-aqueous excipient to form a non-aqueous composition, and then mixing the non-aqueous composition with the aqueous solution.

The pharmaceutical composition prepared by either method can have a shelf-stability of at least 3 months (e.g., 3 months, 6 months, 9 months, 1 year, or more than 1 year). In some embodiments, the pharmaceutical composition, after being stored at 25° C. under 40% RH for 3 months, has at least 90% (e.g., at least 91%, at least 92%, at least 93%, at least 94%, at least 95%, at least 96%, at least 97%, at least 98%, at least 99%, or greater than 99%) of the lipoic acid choline ester or derivatives thereof present in the composition as measured by HPLC. In some embodiments, the pharmaceutical composition, after being stored at 25° C. under 40% RH for 3 months, has 5% or less (e.g., less than 4%, less than 3%, less than 2%, less than 1%, or less than 0.5%) of the lipoic acid choline ester or derivatives thereof been degraded as measured by HPLC.

The pharmaceutical composition can also have favorable profiles of drug related degradant (e.g., total drug related impurities, or amount of a specific drug related impurity) following storage at 25° C. under 40% RH for a certain period of time. Analytical tools (e.g., HPLC) for measuring the amount of drug related degradant in a formulation are known. In some embodiments, the pharmaceutical composition is characterized by having 12% or less (e.g., less than 10%, less than 8%, less than 6%, less than 4%, less than 2%, or less than 1%) total drug related impurities based on area-under-the-curve as determined by HPLC following storage at 25° C. under 40% RH for 3 months. In some embodiments, the pharmaceutical composition is characterized by having 7% or less (e.g., less than 6%, less than 5%, less than 4%, less than 3%, less than 2%, or less than 1%) of a drug related impurity based on area-under-the-curve as determined by HPLC following storage at 25° C. under 40% RH for 3 months, wherein the drug related impurity is characterized by a relative retention time of 1.12 to 1.14. In some embodiments, the pharmaceutical composition is characterized by having 4% or less (e.g., less than 3%, less than 2%, or less than 1%) of a drug related impurity based on area-under-the-curve as determined by HPLC following storage at 25° C. under 40% RH for 3 months, wherein the drug related impurity is characterized by a relative retention time of 0.65 to 0.66.

Concentration of lipoic acid choline ester or derivatives thereof in the pharmaceutical composition can be any concentration of from 1% to 10% (e.g., 1%, 2%, 3%, 4%, 5%, 6%, 7%, 8%, 9%, 10%, or any ranges based on these specified numeric values) by weight of the composition. In some embodiments, the concentration of the lipoic acid choline ester in the pharmaceutical composition is 1%. In some embodiments, the concentration of the lipoic acid choline ester in the pharmaceutical composition is 3%. In some embodiments, the concentration of the lipoic acid choline ester in the pharmaceutical composition is 4%.

The non-aqueous excipient can be an ophthalmically acceptable excipient. In some embodiments, the non-aqueous excipient is non-hydrolytic. In some embodiments, the non-aqueous excipient is substantially miscible with water. In some embodiments, the non-aqueous excipient forms an emulsion upon mixing with water. In some embodiments, the non-aqueous excipient is an ionic liquid (e.g., glycerolcholine).

In some embodiments, the non-aqueous excipient that is substantially miscible with water is an alcohol (e.g., ethanol, sorbitol, propylene glycol, polyethylene glycol, glycerol, or a mixture thereof). In some embodiments, the alcohol is a polyol (e.g., propylene glycol, glycerol, ethylene glycol, diethylene glycol, erythritol, lactitol, maltitol, mannitol, sorbitol, xylitol, pentaerythritol, or sucrose). In some embodiments, the polyol is glycerol. In some embodiments, the polyol is propylene glycol.

In some embodiments, the non-aqueous excipient is a semifluorinated alkane. Semifluorinated alkanes are known, for example, as described in U.S. Patent Application Publication 2013/0046014, the content of which is incorporated by reference in its entirety. Semifluorinated alkanes are linear or branched alkanes some of whose hydrogen atoms have been replaced by fluorine. In some embodiments, the semifluorinated alkanes are composed of at least one non-fluorinated hydrocarbon segment and at least one perfluorinated hydrocarbon segment. In some embodiments, the semifluorinated alkanes have one non-fluorinated hydrocarbon segment attached to one perfluorinated hydrocarbon segment, according to the general formula $F(CF_2)_n(CH_2)_mH$, or two perfluorinated hydrocarbon segments separated by one non-fluorinated hydrocarbon segment, according to the general formula $F(CF_2)_n(CH_2)_m(CF_2)_oF$, wherein n, m, and o are independently selected in the range from 3 to 20.

Concentrations of the non-aqueous excipient (e.g., glycerol) in the pharmaceutical composition can be from 0.1% to 10% (e.g., 0.1%, 0.2, 0.5%, 1%, 2%, 3%, 4%, 5%, 6%, 7%, 8%, 9%, 10%, or any ranges based on these specified numeric values) by weight of the composition. In some embodiments, the non-aqueous excipient is glycerol, and the concentration of glycerol is in the range of 0.1% to 5% (e.g., 0.1%, 0.2%, 0.5%, 1%, 1.5%, 2%, 2.5%, 3%, 3.5%, 4%, 4.5%, 5%, or any ranges based on these specified numeric values) by weight of the composition. In some embodiments, the concentration of glycerol is 0.1%, 0.4%, 1.3%, or 2.7% by weight of the composition.

The pharmaceutical composition can also contain other suitable ingredients. Non-limiting examples of such suitable ingredients include one or more ingredients selected from the group consisting of a biochemically acceptable energy source, a preservative, a buffer agent, a tonicity agent, a surfactant, a viscosity modifying agent, and an antioxidant.

Suitable biochemically acceptable energy source can be any of those known in the art. For example, the biochemical acceptable energy source can be any of those that can facilitate reduction by participating as an intermediate of energy metabolic pathways, particularly the glucose metabolic pathway. Non-limiting examples of suitable biochemically acceptable energy source include amino acids or derivative thereof (e.g., alanine, glycine, valine, leucine, isoleucine, 2-oxoglutarate, glutamate, and glutamine, etc.), a sugar or metabolites thereof (e.g., glucose, glucose-6-phosphate (G6P)), pyruvate (e.g., ethyl pyruvate), lactose, lactate, or derivatives thereof), a lipid (e.g., a fatty acid or derivatives thereof such as mono-, di-, and tri-glycerides and phospholipids), and others (e.g., NADH). Suitable amount of a biochemically acceptable energy source can be in the range of 0.01% to 5% (e.g., 0.05%, 0.1%, 0.2%, 0.5%, 1%, 2%, 3%, 4%, 5%, or any ranges based on these specified numeric values) by weight of the composition. In some embodiments, the biochemical energy source is ethyl pyruvate. In some embodiments, the biochemical energy source is alanine. In some embodiments, the amount of ethyl pyruvate or alanine is in the range of 0.05% to 5% (e.g., 0.05%, 0.1%, 0.2%, 0.5%, 1%, 2%, 3%, 4%, 5%, or any ranges based on these specified numeric values) by weight of the composition. In some embodiments, the amount of alanine is 0.5% by weight of the composition. In any of the embodiments described herein, the biochemically acceptable energy source is in an amount that is ophthalmically acceptable.

Suitable preservatives can be any of those known in the art. Non-limiting examples include benzalkonium chloride (BAK), cetrimonium, chlorobutanol, edetate disodium (EDTA), polyquaternium-1 (Polyquad®), polyhexamethylene biguanide (PHMB), stabilized oxychloro complex (PURITE®), sodium perborate, and SofZia®. Suitable amount of a preservative in the pharmaceutical composition can be in the range of 0.005% to 0.1% (e.g., 0.005, 0.01, 0.02%, 0.05%, 0.1%, or any ranges based on these specified numeric values) by weight of the composition. In some embodiments, the preservative is benzalkonium chloride. In some embodiments, the benzylalkonium chloride is in the amount of 0.005% to 0.1% (e.g., 0.005, 0.01, 0.02%, 0.05%, 0.1%, or any ranges based on these specified numeric values) by weight of the composition. In some embodiments, the benzylalkonium chloride is in the amount of 0.01% by weight of the composition. In any of the embodiments described herein, the preservative is in an amount that is ophthalmically acceptable. In some embodiments, the pharmaceutical composition is free of a preservative. Even though lipoic acid choline ester or a derivative thereof may function as a preservative, as used herein, it is not categorized as a preservative.

Suitable buffer agent can be any of those known in the art that can achieve a desired pH (e.g., described herein) for the pharmaceutical composition. Non-limiting examples include phosphate buffers (e.g., sodium phosphate monobasic monohydrate, sodium phosphate dibasic anhydrous), acetate buffer, citrate buffer, borate buffers, and HBSS (Hank's Balanced Salt Solution). Suitable amount of a buffer agent can be readily calculated based on a desired pH. In any of the embodiments described herein, the buffer agent is in an amount that is ophthalmically acceptable. However, in some embodiments, the pharmaceutical composition does not include a buffer agent. In some embodiments, the pH of the aqueous solution or the final pharmaceutical composition is adjusted with an acid (e.g., hydrochloride acid) or a base (e.g., sodium hydroxide) to the desired pH range (e.g., as described herein). Even though some compounds that normally would not be routinely used as buffer agents, such as alanine, may still have the capacity as being a buffer agent; but as used herein, they are not categorized as buffer agents.

Suitable tonicity agent can be any of those known in the art. Non-limiting examples include sodium chloride, potassium chloride, mannitol, dextrose, glycerin, propylene glycol and mixtures thereof. Suitable amount of tonicity agent in the pharmaceutical composition is any amount that can achieve an osmolality of 200-460 mOsm (e.g., 260-360 mOsm, or 260-320 mOsm). In some embodiments, the pharmaceutical composition is an isotonic composition. In some embodiments, the amount of a tonicity agent (e.g., sodium chloride) is 0.1% to 5% (e.g., 0.1%, 0.5%, 1%, 2%, 3%, 4%, 5%, or any ranges based on these specified numeric values) by weight of the composition. In any of the embodiments described herein, the tonicity agent is in an amount that is ophthalmically acceptable.

Suitable surfactant can be any of those known in the art, including ionic surfactants and nonionic surfactants. Non-limiting ionic surfactants include ammonium lauryl sulfate, sodium lauryl sulfate, sodium laureth sulfate, sodium myreth sulfate, dioctyl sodium sulfosuccinate, perfluorooctanesulfonate, perfluorobutanesulfonate, linear alkylbenzene sulfonates, sodium lauroyl sarcosinate, perfluorononanoate, perfluorooctanoate, octenidine dihydrochloride, cetyl trimethylammonium bromide, cetyl trimethylammonium chloride, cetylpyridinium chloride (CPC), benzalkonium chloride (BAC), benzethonium chloride (BZT), dimethyldioctadecylammonium chloride, cetrimonium bromide, dioctadecyldimethylammonium bromide, sultains (e.g., cocamidopropyl hydroxysultaine), phosphates (e.g., lecithin), and betaines, (e.g., cocamidopropyl betaine).

Non-limiting examples of useful nonionic surfactants include polyoxyethylene fatty esters (e.g., polysorbate 80 [poly(oxyethylene)sorbitan monooleate], polysorbate 60 [poly(oxyethylene)sorbitan monostearate], polysorbate 40 [poly(oxyethylene)sorbitan monopalmitate], poly(oxyethylene)sorbitan monolaurate, poly(oxyethylene)sorbitan trioleate, or polysorbate 65 [poly(oxyethylene)sorbitan tristearate]), polyoxyethylene hydrogenated castor oils (e.g., polyoxyethylene hydrogenated castor oil 10, polyoxyethylene hydrogenated castor oil 40, polyoxyethylene hydrogenated castor oil 50, or polyoxyethylene hydrogenated castor oil 60), polyoxyethylene polyoxypropylene glycols (e.g., polyoxyethylene (160) polyoxypropylene (30) glycol [Pluronic F681], polyoxyethylene (42) polyoxypropylene (67) glycol [Pluronic P123], polyoxyethylene (54) polyoxypropylene (39) glycol [Pluronic P85], polyoxyethylene (196) polyoxypropylene (67) glycol [Pluronic F1271], or polyoxyethylene (20) polyoxypropylene (20) glycol [Pluronic L-441]), polyoxyl 40 stearate, sucrose fatty esters, and a combination thereof. In some embodiments, the surfactant is polysorbate 80. Suitable amount of surfactant in the pharmaceutical composition can be in the range of 0.01% to 5% (e.g., 0.05, 0.1, 0.2%, 0.5%, 1%, 2%, 3%, 4%, 5%, or any ranges based on these specified numeric values) by weight of the composition. In some embodiments, the surfactant is polysorbate 80, and the amount of polysorbate 80 is in the range of 0.05% to 5% (e.g., 0.05, 0.1, 0.2%, 0.5%, 1%, 2%, 3%, 4%, 5%, or any ranges based on these specified numeric values) by weight of the composition. In some embodiments, the amount of polysorbate 80 is 0.5% by weight of the composition. In any of the embodiments described herein, the surfactant is in an amount that is ophthalmically acceptable. However, in some embodiments, the pharmaceutical composition is free of a surfactant. Even though lipoic acid choline ester or a derivative thereof may function as a surfactant, as used herein, it is not categorized as a surfactant.

Suitable viscosity modifying agent can be any of those known in the art. Non-limiting examples include carbopol gels, cellulosic agents (e.g., hydroxypropyl methylcellulose), polycarbophil, polyvinyl alcohol, dextran, gelatin glycerin, polyethylene glycol, poloxamer 407, polyvinyl alcohol and polyvinyl pyrrolidone and mixtures thereof. Suitable amount of viscosity modifying agent can be in the range of 0.1% to 5% (e.g., 0.1%, 0.5%, 1%, 2%, 3%, 4%, 5%, or any ranges based on these specified numeric values) by weight of the composition. In any of the embodiments described herein, the viscosity modifying agent is in an amount that is ophthalmically acceptable. In some embodiments, the pharmaceutical composition is free of a viscosity modifying agent (e.g., a polymeric viscosity modifying agent such as hydroxypropyl methylcellulose).

Suitable antioxidant can be any of those known in the art. In some embodiments, the redox potential of the antioxidant is less than 0.5 my (e.g., less than 0.4 my, less than 0.3 my, less than 0.2 my, or less than 0.1 my). In some embodiments, the redox potential of the antioxidant is less than 0.28 my, the redox potential for dihydrolipoic acid (DHLA). Non-limiting examples include ascorbic acid, L-ascorbic acid stearate, alphathioglycerin, ethylenediaminetetraacetic acid, erythorbic acid, cysteine hydrochloride, N-acetylcysteine, L-carnitine, citric acid, tocopherol acetate, potassium dichloroisocyanurate, dibutylhydroxytoluene, 2,6-di-t-butyl-4-methylphenol, soybean lecithin, sodium thioglycollate, sodium thiomalate, natural vitamin E, tocopherol, ascorbyl pasthyminate, sodium pyrosulfite, butylhydroxyanisole, 1,3-butylene glycol, pentaerythtyl tetrakis [3-(3,5-di-t-butyl-4-hydroxyphenyl)]propionate, propyl gallate, 2-mercaptobenzimidazole and oxyquinoline sulfate. Suitable amount of antioxidant can be in the range of 0.1% to 5% (e.g., 0.1%, 0.5%, 1%, 2%, 3%, 4%, 5%, or any ranges based on these specified numeric values) by weight of the composition. In any of the embodiments described herein, the antioxidant is in an amount that is ophthalmically acceptable.

In some embodiments, the pharmaceutical composition is characterized by one or more of the following:
(a) having a concentration of the lipoic acid choline ester from 1% to 10% (e.g., 1%, 1.5%, 3%, 4%, 5%, or any ranges between the specified numeric values) by weight of the composition;
(b) having a concentration of a preservative (e.g., benzalkonium chloride) of 0.005% to 0.1% (e.g., 0.01%) by weight of the composition;
(c) having a biochemical energy source (e.g., alanine) of 0.1% to 5% (e.g., 0.5%) by weight of the composition; and
(d) having a concentration of glycerol of 0.5% to 5% (e.g., 2.7%) by weight of the composition.

In some embodiments, the lipoic acid choline ester in the pharmaceutical composition has a counter ion selected from the group consisting of chloride, bromide, iodide, sulfate, methanesulfonate, nitrate, maleate, acetate, citrate, fumarate, hydrogen fumarate, tartrate (e.g., (+)-tartrate, (−)-tartrate, or a mixture thereof), succinate, benzoate, and anions of an amino acid such as glutamic acid. In some embodiments, the counter ion is chloride.

In some embodiments, the pharmaceutical composition contains a non-aqueous excipient, which is glycerol in a concentration of 2.7% by weight of the composition. In some embodiments, the concentration of glycerol is 3% by weight of the composition.

In some embodiments, the pharmaceutical composition consists essentially of 0.025% by weight of edetate disodium dehydrate, 1.3% by weight of glycerin, 0.5% by weight of alanine, 0.01% by weight of benzalkanium chloride, 1% by weight of lipoic acid choline ester, and water, wherein the pH of the pharmaceutical composition is 4.3 to 4.7.

In some embodiments, the pharmaceutical composition consists essentially of 0.025% by weight of edetate disodium dehydrate, 0.4% by weight of glycerin, 0.5% by weight of alanine, 0.01% by weight of benzalkanium chloride, 3% by weight of lipoic acid choline ester, and water, wherein the pH of the pharmaceutical composition is 4.3 to 4.7.

In some embodiments, the pharmaceutical composition consists essentially of 0.025% by weight of edetate disodium dehydrate, 0.1% by weight of glycerin, 0.5% by weight of alanine, 0.01% by weight of benzalkanium chloride, 4% by weight of lipoic acid choline ester, and water, wherein the pH of the pharmaceutical composition is 4.4 to 4.6.

Mixing LACE with a Non-Aqueous Excipient

As stated above, the pharmaceutical compositions described herein can be formed by premixing the therapeutically effective amount of lipoic acid choline ester with a non-aqueous excipient to form a non-aqueous composition. The non-aqueous composition can then be further mixed with an aqueous solution, e.g., to form an ophthalmic formulation. In some aspects, the invention also provides a system or method of long-term storage of the pharmaceutical composition by storing the non-aqueous composition separately from the aqueous solution, for example, in a two-part device (e.g., as described herein) or in a kit. The separately stored non-aqueous composition can then be mixed with the aqueous solution to form an "activated" formulation prior to use.

The non-aqueous composition can be a solution, an emulsion, or a suspension formed by mixing lipoic acid choline ester and the non-aqueous excipient. The mixing can be conducted under heat for a sustained period of time. In some embodiments, the mixing is conducted at a temperature of 20° C. to 100° C. (e.g., 20° C., 30° C., 40° C., 50° C., 60° C., 70° C., 80° C., 90° C., 100° C., or any ranges based on these specified numeric values) for a period of 1 hour to 24 hours (e.g., 1 hour, 2 hours, 4 hours, 6 hours, 8 hours, 10 hours, 12 hours, 14 hours, 16 hours, 18 hours, 20 hours, 22 hours, 24 hours, or any ranges based on these specified numeric values). In some embodiments, the mixing is conducted at a temperature of 37° C. to 80° C. In some embodiments, the mixing is carried out for 8 hours.

In some embodiments, the non-aqueous composition is a solution. In some embodiments, the solution contains lipoic acid choline ester. In some embodiments, the solution contains a derivative of lipoic acid choline ester (e.g., a reaction product formed from lipoic acid choline ester and a non-aqueous excipient (e.g., propylene glycol or glycerol). The concentration of lipoic acid choline ester or derivatives thereof in the solution can be up to the solubility limit in the non-aqueous excipient (e.g., propylene glycol or glycerol). In some embodiments, the concentration of lipoic acid choline ester or derivatives thereof is in a range of 0.1% to 40% (e.g., 1%, 5%, 10%, 15%, 20%, 25%, 30%, 35%, 40%, or any ranges based on these specified numeric values) by weight of the solution.

Mixing the Non-Aqueous Composition with an Aqueous Solution

The non-aqueous compositions described herein can be mixed with an aqueous solution having a pH of 4 to 8 (e.g., 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, or any ranges based on these specified numeric values) to form an ophthalmic formulation. In some embodiments, mixing the non-aqueous composition does not substantially change the pH of the aqueous solution, i.e., the ophthalmic formulation also has a pH of 4 to 8. In some embodiments, the ophthalmic formulation has a pH of 4 to 6 (e.g., 4.2, 4.4, 4.6, 4.8, 5.0, 5.2, 5.4, 5.6, 5.8, 6.0, or any ranges based on these specified numeric values). In some embodiments, the ophthalmic formulation has a pH of 4.2 to 4.7 (e.g., 4.5).

The ophthalmic formulations can be sterilized. In some embodiments, the non-aqueous composition is sterilized before mixing with the aqueous solution. In some embodiments, the aqueous solution is also sterilized. In some embodiments, the non-aqueous composition is mixed with the aqueous solution (e.g., a sterilized aqueous solution, or a non-sterilized aqueous solution) and then sterilized.

The ophthalmic formulation can include one or more ingredients selected from the group consisting of a biochemically acceptable energy source, a preservative, a buffer agent, a tonicity agent, a surfactant, a viscosity modifying agent, and an antioxidant. Suitable biochemically acceptable energy sources, preservatives, buffer agents, tonicity agents, surfactants, viscosity modifying agents, and antioxidants are those described herein. In some embodiments, the one or more ingredients are mixed in the aqueous solution before mixing with the non-aqueous composition. In some embodiments, the one or more ingredients are mixed in the non-aqueous composition before mixing with the aqueous solution. Suitable amounts of biochemically acceptable energy sources, preservatives, buffer agents, tonicity agents, surfactants, viscosity modifying agents, and antioxidants are also described herein. However, in any of the embodiments described herein, the ophthalmic formulation can also be free of a buffer agent, a surfactant, a viscosity modifying agent, a preservative, or a combination thereof.

In some embodiments, the ophthalmic formulation is characterized by one or more of:
(a) having a concentration of the lipoic acid choline ester or derivatives thereof from 1% to 10% (e.g., 1%, 1.5%, 3%, 4%, 5%, or any ranges based on the specified numeric values) by weight of the formulation;
(b) having a concentration of a preservative (e.g., benzalkonium chloride) 0.005% to 0.1% (e.g., 0.01%) by weight of the formulation;
(c) having a pH of 4 to 6 (e.g., 4.2, 4.4, 4.6, 4.8, 5.0, 5.2, 5.4, 5.6, 5.8, 6.0, or any ranges based on these specified numeric values);
(d) having a biochemical energy source (e.g., alanine) of 0.1% to 5% (e.g., 0.5%) by weight of the formulation;
(e) having a concentration of glycerol of 0.5% to 5% (e.g., 2.7%) by weight of the formulation; and
(f) having a shelf-life stability of greater than 3 months (e.g., 3 months, 6 months, 9 months, or 12 months).

In some embodiments, the ophthalmic formulation contains a non-aqueous excipient, which is glycerol in a concentration of 2.7% by weight of the composition. In some embodiments, the concentration of glycerol is 3% by weight of the formulation.

In some embodiments, the ophthalmic formulation consists essentially of 0.025% by weight of edetate disodium dehydrate, 1.3% by weight of glycerin, 0.5% by weight of alanine, 0.01% by weight of benzalkanium chloride, 1% by weight of lipoic acid choline ester or derivatives thereof, and water, wherein the pH of the ophthalmic formulation is 4.3 to 4.7.

In some embodiments, the ophthalmic formulation consists essentially of 0.025% by weight of edetate disodium dehydrate, 0.4% by weight of glycerin, 0.5% by weight of alanine, 0.01% by weight of benzalkanium chloride, 3% by weight of lipoic acid choline ester or derivatives thereof, and water, wherein the pH of the ophthalmic formulation is 4.3 to 4.7.

In some embodiments, the ophthalmic formulation consists essentially of 0.025% by weight of edetate disodium dehydrate, 0.1% by weight of glycerin, 0.5% by weight of alanine, 0.01% by weight of benzalkanium chloride, 4% by weight of lipoic acid choline ester or derivatives thereof, and water, wherein the pH of the ophthalmic formulation is 4.4 to 4.6.

Storage of LACE Formulation

As lipoic acid choline ester can be susceptible to hydrolysis and light induced oxidation, in some embodiments, the invention provides a method for storing lipoic acid choline ester in a non-aqueous environment, an oxygen free environment, and/or with reduced light exposure. In some embodiments, the lipoic acid choline ester is stored in a non-aqueous environment. In some embodiments, the lipoic acid choline ester is stored in the non-aqueous environment as a lyophilized powder. In some embodiments, the lipoic acid choline ester is stored in the non-aqueous environment as a non-aqueous composition (e.g., as described herein). In some embodiments, the lipoic acid choline ester is stored in a non-aqueous environment in an opaque container. In some embodiments, the non-aqueous environment is substantially oxygen free.

In some embodiments, the lipoic acid choline ester is stored in an aqueous environment (e.g., after mixing a non-aqueous composition with an aqueous solution), wherein the aqueous environment is free of oxygen. In some embodiments, the lipoic acid choline ester is stored in the aqueous environment with reduced light exposure (e.g., in an opaque container).

In some embodiments, the invention also provides a system for storing a pharmaceutical composition comprising an active ingredient in an aqueous solution, wherein the active ingredient (e.g., lipoic acid choline ester or derivatives thereof) is susceptible to hydrolysis in the aqueous solution.

In some embodiments, the system comprises a first compartment, a second compartment, and a seal separating the first and second compartments, wherein the first compartment comprises a non-aqueous composition comprising the active ingredient (e.g., lipoic acid choline ester or derivatives thereof), the second compartment comprises an aqueous solution. In some embodiments, the active ingredient in the first compartment is in a solid form (e,g., a powder, e.g., a lyophilized powder). In some embodiments, the active ingredient in the first compartment is mixed with a non-aqueous excipient (e.g., as described herein). In some embodiments, the system is activated upon breaking the seal and mixing the non-aqueous solution with the aqueous solution.

Figure 4:
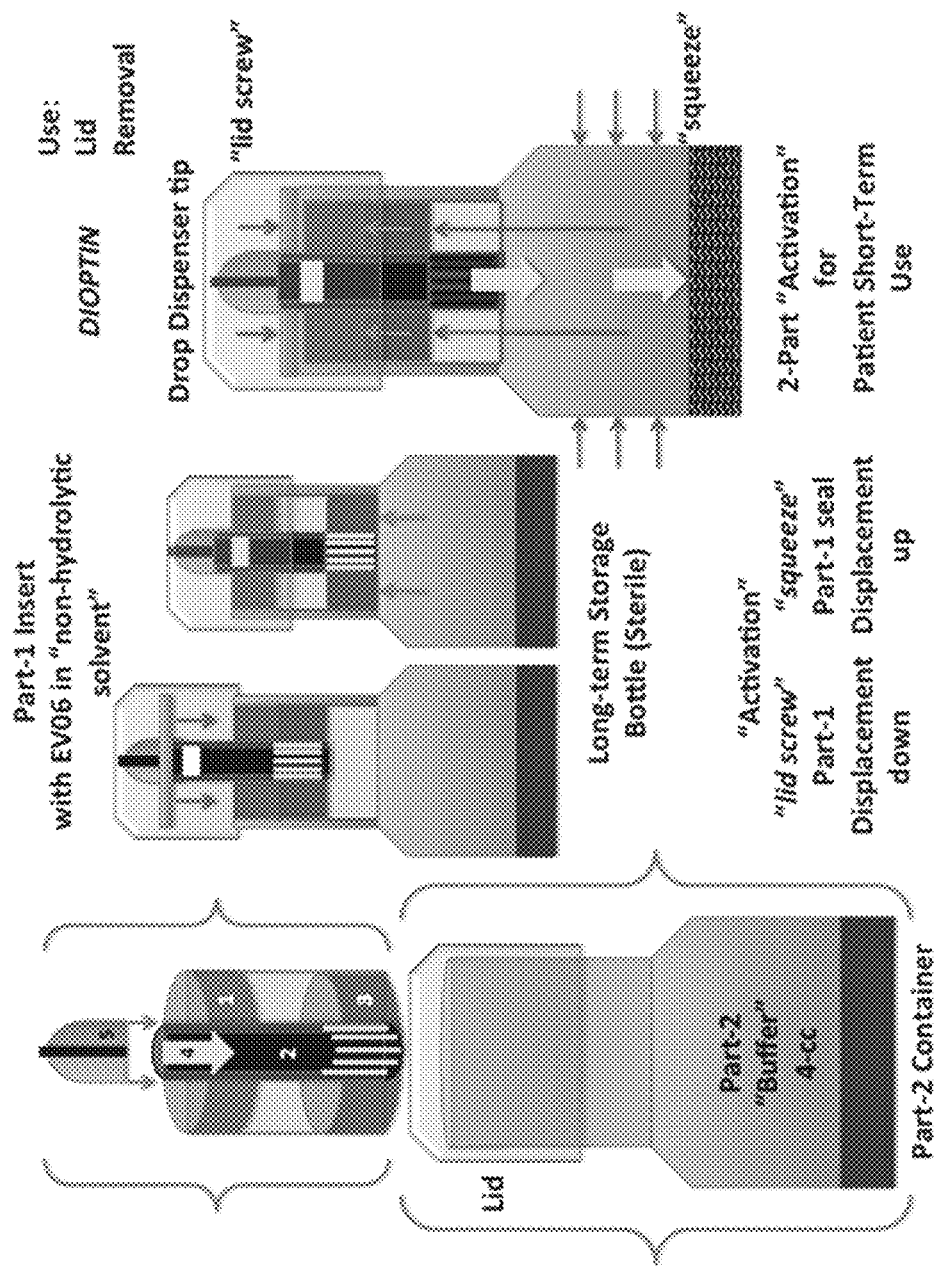
FIG. 4 shows a design of a two-part eye drop bottle with an insert that can be used for long term storage of lipoic acid choline ester formulations.

An example of the system is a modified eye drop bottle shown in FIG. 4. The eye drop bottle contains two parts, part 1 (includes the first compartment and the seal, shown as an insert in FIG. 4) and part 2 (includes the second compartment) (see FIG. 4), with the compartments separated from each other prior to formation of final formulation for patient activation and use. In some embodiments, part 1 of the eye drop bottle contains any of the non-aqueous compositions described herein (e.g., lipoic acid choline ester or derivatives thereof mixed with glycerol). In some embodiments, part 1 of the eye drop bottle contains a non-aqueous composition comprising an active ingredient (e.g., a peptide) that is susceptible to hydrolysis in an aqueous solution.

In some embodiments, part 1 of the eye drop bottle contains lipoic acid choline ester or derivatives thereof in glycerol (e.g., 150 mg LACE/1.03 uL glycerol). In some embodiments, part 2 of the eye drop bottle contains an aqueous solution (4.8 mL) having the following excipients: 0.01% by weight of Benzalkonium Chloride; 2.6% by weight of Glycerin, USP; and 0.5% by weight of Alanine, USP, wherein the pH of the solution is 4.5±0.2.

The insert separates the non-aqueous composition from part 2 until activation, which allows long-term storage until short-term ocular treatment is started. In some embodiments, the insert includes a main insert stationary holder; an inner tube; and a lower seal, wherein the inner tube is configured to contain the non-aqueous composition and the lower seal is configured to prevent contact of the non-aqueous composition with the aqueous solution. In some embodiments, the eye drop bottle includes a dropper tip, which seals the insert. In some embodiments, the eye drop bottle is configured such that compressing or squeezing the bottle is sufficient to move the lower seal upward, whereby exposing the inner tube perforations to release the non-aqueous composition into the aqueous solution.

In any of the embodiments described above, the non-aqueous composition comprising the active pharmaceutical ingredient (e.g., lipoic acid choline ester or derivatives thereof), prior to releasing into the aqueous solution, is shelf-stable for at least 3 months (e.g., 6 months, 9 months, 12 months, 2 years, or more than 2 years). In some embodiments, the non-aqueous composition is characterized by having 2% or less (e.g., 1.5%, 1%, 0.5%, or 0.2%) of the active pharmaceutical ingredient degraded. In some embodiments, the non-aqueous composition is characterized by having 10% or less (e.g., 9%, 8%, 7%, 6%, 5%, 4%, 35, 2%, 1%, 0.5%, or 0.2%) of the active pharmaceutical ingredient degraded. In some embodiments, the pharmaceutical composition formed by releasing the non-aqueous composition into the aqueous solution is shelf-stable for at least 3 months (e.g., 6 months, 9 months, or 12 months).

In some embodiments, the invention also provides a method of storing an active ingredient that is susceptible to hydrolysis in an aqueous solution, the method comprising (a) providing the active ingredient in a first compartment; (b) providing the aqueous solution in a second compartment; and (c) separating the first and second compartments, e.g., with a seal, wherein the active ingredient in the first compartment is not in contact with the aqueous solution until just prior to usage, e.g., by breaking the seal. In some embodiments, the active ingredient in the first compartment is mixed with a non-aqueous excipient (e.g., as described herein). In some embodiments, the active ingredient is lipoic acid choline ester or derivatives thereof, or a peptide. Suitable methods for configuring the first compartment and the second compartment include those described herein.

Methods of Treatment

The pharmaceutical compositions comprising lipoic acid choline ester or derivatives thereof (e.g., as described herein) can be employed in a method for treating or preventing a disease or disorder associated with oxidative damage. Diseases or disorders associated with oxidative damage are known.

In some embodiments, the invention provides a method of treating an ocular disease in a subject in need thereof, comprising administering to a lens or an eye of the subject a therapeutically effective amount of any of the pharmaceutical compositions described herein. In some embodiments, the ocular diseases are presbyopia, cataract, macular degeneration (including age-related macular degeneration), retinopathies (including diabetic retinopathy), glaucoma, or ocular inflammations. In some embodiments, the ocular disease is presbyopia.

Suitable amount of pharmaceutical compositions for the methods of treating or preventing an ocular disease herein can be any therapeutically effective amount. In some embodiments, the method comprises administering to the lens or eye of the subject an amount of the pharmaceutical composition effective to increase the accommodative amplitude of the lens by at least 0.1 diopters (D) (e.g., 0.1, 0.2, 0.5, 1, 1.2, 1.5, 1.8, 2, 2.5, 3, or 5 diopters). In some embodiments, the method comprises administering to the lens or eye of the subject 1-5 drops (about 40 uL per drop) of the pharmaceutical composition. In some embodiments, the lens or eye of the subject is treated with the pharmaceutical composition 1, 2, 3, 4, 5, or more than 5 times a day, each time with 1-5 drops (about 40 uL per drop). In some embodiments, the lens or eye of the subject is treated with the pharmaceutical composition 1, 2, 3, 4, 5, or more than 5 drops each time. In some embodiments, the lens or eye of the subject is treated with the pharmaceutical composition herein twice or three times per day, each time with 1 or 2 drops (about 40 uL per drop).

The methods include preventative methods that can be performed on patients of any age. The methods also include therapeutic methods that can be performed on patients of any age, particularly patients that are 20, 25, 30, 35, 40, 45, 50, 52, 55, 57, 60, 70, 75, or 80 years of age or older.

The following examples are illustrative and do not limit the scope of the claimed embodiments.

EXAMPLES

Example 1

Synthesis of LACE Chloride

A two-step synthesis of lipoic acid choline ester chloride is described below.

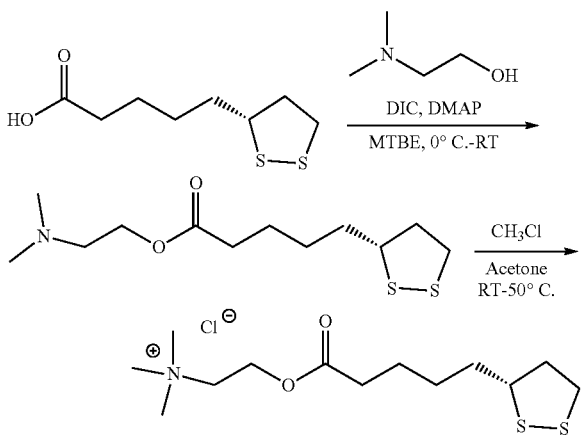

R-lipoic acid (5 g, 24.3 mmol), dimethylaminoethanol, (2.37 g, 26.7 mmol) and DMAP (0.9 g, 7.3 mmol) were suspended in MTBE (40 mL) at room temperature under nitrogen. The reaction mixture was cooled to 0° C. and DIC (3.36 g, 26.7 mmol) in MTBE (20 mL) was added. After addition, the mixture was slowly warmed to room temperature and stirred for minimum 12 hours. The reaction was monitored by TLC (5% MeOH/CH$_2$Cl$_2$). Reaction mixture was filtered, washed with MTBE, and purified via flash chromatography to give yellow oil (3.3 g, 10.1 mmol).

Lipoate obtained above (0.5 g, 1.8 mmol) was suspended in acetone (1.8 mL) and CH$_3$Cl (1.8 mL, 1.0 in MTBE) was added. The reaction was heated under nitrogen at 50° C. in a sealed tube overnight. HPLC showed 95% conversion.

Example 2

Studies on Stability of LACE Formulations

Various lipoic acid choline ester formulations were tested for stabilities.
Equipment
The HPLC systems that were used in the performance of the HPLC assays were qualified by CGMP with IQ, OQ and PQ. Each system that was used consisted of a Waters 2695 Separations Module and Waters 2487 Dual λ Absorbance Detector.

The following additional equipments were used in the experiments:
Mettler AE163 Balance, E-000,902
Mettler AE200 Balance, E-000,903
Mettler PB3002 Balance, E-000,904
Fisher ARSO Accumet pH Meter, E-000,726
Precision Systems 5004 J.-LOsmette Osmometer, E-000, 705, E-000,800
Millipore A-10 Advantage Purified Water System, E-000, 723
Container Closures
3 mL white bottles:
3 cc LDPE Cylinder Round Bottle, Resin: Dupont 20-6064, Color: White, PCC PEC17030 (WX in Mix), Alcan Packaging, PN: 20319-137 (BPN-000,688)
3 cc LDPE Cylinder Round Bottle, Resin: Chevron PE 5104 Color: White WX0200, Alcan; Packaging, PN: 20319-007 (BPN-000,441)
3 mL natural bottles:
3 cc Clylinder Round Bottle, Resin: LDPE Chevron Phillips PE 5104, Color: Natural, Additive: PCC Lube-ZnSt 110445 S068, Alcan Packaging, PN: 20319-006 (BPN-000,653)
Tips:
8 mm Controlled Dropper Tip 0.020 Needle, Natural, Resin: LLDPE Dow Dowlex 2517, Alcan Packaging, PN: 12208-0AA (BPN-000,443)
8 mm Controlled Dropper Tip, 0.020 Needle, Natural, Resin: LDPE Dupont 20-6064, Alcan Packaging, PN: 12208-015 (BPN-000,492B)
Caps:
08/425 Dropper Tip Cap, Resin: PP Sunoco FT-120-W2 Color: White PCC C10054C, Alcan Packaging, PN: 15055-201 (BPN-000,442)
Methods
The pH was measured following USP/NF <791> and SOP-00273. The osmolality was measured following USP/NF <785> and SOP-00084.

The HPLC method to analyze LACE Chloride used a Phenomenex Luna CN column with a 5 um particle size, 100 A pore size, 2.0 mm inner diameter, and 50 mm length (PN: 00B-4255-B0). The mobile phase consisted of 50% of 0.1 M Sodium Acetate and 50% Acetonitrile. The flow rate was 1.0 mL/min, the detection wavelength was 225 nm, the column temperature was 40° C., the injection volume was 20 uL, and the run time was 50 minutes. The working LACE chloride concentration was 0.1 mg/mL and plastic HPLC vials were used for the analysis.

For the final stability screen on LACE chloride formulations (BCL457-180, BCL471-189, BCL483-079, BCL483-165, BCL489-027) the mobile phase concentration was errantly prepared to 0.01 M Sodium Acetate. This resulted in wide LACE peaks with a longer retention time, but did not seem to affect the results. The LACE standard was consistent with the LACE in the samples.
Formulations BCL442-110 B-H
Table 1 shows the detailed formulations of LACE chloride ophthalmic formulations at pH 5.5 and 7.0 (BCL442-110).

TABLE 1

| | LACE Chloride Ophthalmic Formulations in Phosphate Buffer | | | | | |
|---|---|---|---|---|---|---|
| Component | BCL442-110B | BCL442-110C | BCL442-110D | BCL442-110F | BCL442-110G | BCL442-110H |
| Sodium Phosphate Monobasic, | 0.07% | 0.07% | 0.07% | 0.07% | 0.07% | 0.07% |
| Sodium Phosphate Dibasic, | 0.13% | 0.13% | 0.13% | 0.13% | 0.13% | 0.13% |
| Glycerin | 1.5% | 0.8% | 0% | 1.5% | 0.8% | 0% |
| Edetate Disodium, | 0.10% | 0.10% | 0.10% | 0.10% | 0.10% | 0.10% |
| Benzalkonium Chloride | 0.01% | 0.01% | 0.01% | 0.01% | 0.01% | 0.01% |
| Alanine | 0.10% | 0.10% | 0.10% | 0.10% | 0.10% | 0.10% |
| LACE Chloride | 1.5% | 3.0% | 5.0% | 1.5% | 3.0% | 5.0% |

The pH, osmolality, appearance, and LACE chloride concentration were measured in solutions containing LACE chloride at 1.5%, 3.0%, and 5.0% at pH 5.5 or pH 7.0. The LACE chloride assay was performed four days after preparation. The solutions showed that the LACE chloride is not very stable at pH 7 over four days from the time of preparation until the assay was performed. But the solutions at pH 5.5 resulted in a percent recovery from 86% to 109%, which showed that low pH is more stable for LACE chloride formulations.

Formulations BCL448-053 C and D

The detailed LACE chloride ophthalmic formulations in citrate buffer (BCL448-053) are described in Table 2:

TABLE 2

LACE Chloride Ophthalmic Formulations in Citrate Buffer

| Component | BCL448-053 C (DA-000, 207) | BCL448-053 D (DA-000, 208) |
|---|---|---|
| Citric Acid | 0.50% | 0.50% |
| Glycerin | 0.75% | 0.40% |
| Edetate Disodium, Dihydrate | 0.10% | 0.10% |
| Benzalkonium Chloride | 0.01% | 0.01% |
| Propylene Glycol | 0.75% | 0.40% |
| Alanine | 0.10% | 0.10% |
| LACE Chloride | 1.5% | 3.0% |
| pH Target | 5.5 | 5.5 |

The solutions were tested at the time of preparations and after storage at 5° C. (ambient RH), 25° C. (40% RH), 40° C. (not more than (NMT) 25% RH) and 57° C. (ambient RH) for three months. The solutions were evaluated for LACE chloride concentration to determine stability of LACE over time. The 1.5% LACE chloride solution stored at 5° C. was the only solution that showed no significant change with recovery of 97.0% of LACE after 3 months.

Formulation BCL457-180 D and E

The details of LACE chloride ophthalmic formulations with no buffer, with or without polysorbate 80 (BCL457-180) are shown in Table 3.

TABLE 3

LACE Chloride Ophthalmic Formulations with No Buffer

| Component | BCL457-180 D (DA-000, 294) | BCL457-180 E (DA-000, 295) |
|---|---|---|
| Glycerin | 2.0% | 2.0% |
| Edetate Disodium, Dihydrate | 0.025% | 0.025% |
| Benzalkonium Chloride | 0.01% | 0.01% |
| Polysorbate 80 | 0.0% | 0.5% |
| Alanine | 0.5% | 0.5% |
| Lipoic Acid Choline Ester Chloride Salt | 1.0% | 1.0% |

The solutions were tested at the time of preparations and after storage at 5° C. (ambient RH), 25° C. (40% RH), 40° C. (NMT 25% RH) and 57° C. (ambient RH) for three months.

The results show that the formulations are stable for LACE Chloride potency for 3 months at 5° C. and 25° C./40% RH. The solutions at 40° C./NMT 25% RH show potency less than 90% of initial after two months. There is no significant stability difference observed between formulations with and without polysorbate 80.

Example 3

LACE Formulation with Propylene Glycol

A solution of LACE chloride in propylene glycol was prepared to determine its stability. A solution of 1.0% LACE chloride in propylene glycol was prepared and stored at −20° C. (ambient RH), 5° C. (ambient RH), and 25° C. (40% RH). The solutions were tested for LACE chloride potency after storage for 3 months.

The results show that LACE chloride is not stable in propylene glycol after 3 months storage at 5° C. and 25° C. In these samples, HPLC analysis (using the method described in Example 2) a peak with relative retention time (RRT) of approximately 0.73. For the solution stored at room temperature, the LACE chloride is completely converted to this peak. No additional peaks are detected. The peak at 0.73 RRT is not detected in the LACE chloride solutions in citrate buffer.

Example 4

Three Month Stability Results

Formulations

Three formulations LACE Ophthalmic Solution, 10 mg/mL (1%); 30 mg/mL (3%); and 40 mg/mL (4%) were prepared and tested for stability.

The 1% LACE solution:
0.025% by weight of edetate disodium dehydrate,
1.3% by weight of glycerin,
0.5% by weight of alanine,
0.01% by weight of benzalkanium chloride,
1% by weight of lipoic acid choline ester,
water, and
sodium hydroxide (1N) and/or HCl (1N) to adjust the pH to be 4 to 5.

The 3% LACE solution:
0.025% by weight of edetate disodium dehydrate,
0.4% by weight of glycerin,
0.5% by weight of alanine,
0.01% by weight of benzalkanium chloride,
3% by weight of lipoic acid choline ester,
water, and
sodium hydroxide (1N) and/or HCl (1N) to adjust the pH to be 4 to 5.

The 4% LACE solution:
0.025% by weight of edetate disodium dehydrate,
0.1% by weight of glycerin,
0.5% by weight of alanine,
0.01% by weight of benzalkanium chloride,
4% by weight of lipoic acid choline ester,
water, and
sodium hydroxide (1N) and/or HCl (1N) to adjust the pH to be 4 to 5.

HPLC Methods
Equipment:
Waters 2695 Separation Module or equivalent containing a pump capable of delivering a gradient flow rate of 1.0 mL/min or equivalent and an autosampler.
Waters 2987 Multi wavelength Detector or single wavelength detector capable of detection at 225 nm or equivalent.
Column: YMC Pack ODS AQ, 250×4.6 mm, PN: AQ125052546WT
Reagents:
Acetonitrile, HPLC grade or equivalent
Methanol, HPLC grade or equivalent Sodium Phosphate Monobasic Monohydrate, USP grade or equivalent
1-Heptane Sulfonic Acid, Sodium Salt, HPLC grade or equivalent
Triethylamine, HPLC grade or equivalent Phosphoric Acid, NF grade or equivalent
Purified Water
Analytical Balance
Various Class A volumetric flasks
Various Class A pipets Various graduated cylinders HPLC vials
   HPLC System Parameters:
Column: YMC Pack ODS AQ, 250×4.6 mm, 5 um, 12 nm, PN: AQ125052546WT
Mobile Phase:
A: 0.05 M Sodium Phosphate, 0.005 M 1-Heptane Sulfonic Acid Sodium Salt, 0.2% Triethylamine, pH 4.5 (±0.2) (adjusted with Phosphoric Acid)
D: Acetonitrile
Gradient:

| Time (min) | % A | % D |
|---|---|---|
| 0 | 90 | 10 |
| 29.0 | 50 | 50 |
| 30.0 | 50 | 50 |
| 30.5 | 90 | 10 |
| 50.0 | 90 | 10 |

Flow rate: 1.0 mL/min
Wavelength: 225 nm
Column Temperature: 60° C.
Injection Volume: 10 uL (Potency), 50 uL (RS)
Approximate Run Time*: 50 min
Approximate Retention Time*: 21 min
*The run time and the retention time may vary based on the age of the column and the type of the instrument used
Needle Wash Water:Acetonitrile (90:10)
Diluent 0.05 M Sodium Phosphate
Results The formulations were stored at four different conditions, i.e., 5° C. under ambient RH; 25° C. under 40% RH; 40° C. under not more than 25% RH; and −20° C. under ambient RH. Samples were taken at time 0, 1 month, and 3 months for measurement of EDTA content, BAK content, pH, and LACE potency. The results are shown in Tables 4-7 below. Appearance tests were also done at time 0, 1 month, and 3 months (see Table 8). Drug related impurities were analyzed by HPLC. Tables 9A-9D show the amount of drug related impurities formed at time 0, 1 month, and 3 months (only impurities with an amount greater than 0.05% are reported in the tables).

TABLE 4

EDTA Assay Results

| | | Formulation | | | |
|---|---|---|---|---|---|
| | | EV06 Ophthalmic Solution, Placebo | EV06 Ophthalmic Solution, 10 mg/mL | EV06 Ophthalmic Solution, 30 mg/mL | EV06 Ophthalmic Solution, 40 mg/mL |
| | | | Lot Number | | |
| Specification | | BCL545-129A 80.0% to 120.0% | Lot BCL545-129B 80.0% to 120.0% | Lot BCL545-129C 80.0% to 120.0% | Lot BCL545-129D 80.0% to 120.0% |
| 5 C./Ambient RH | 0 | 97.8% | 98.9% | 98.5% | 98.20% |
| | 1 | 101.0% | 100.4% | 100.1% | 99.10% |
| | 3 | 99.3% | 98.2% | 99.7% | 98.3%, 101.0% |
| 25 C./40% RH | 1 | 102.8% | 100.5% | 100.1% | 98.80% |
| | 3 | 99.5% | 96.5% | 93.9% | 85.4%, 85.1% |
| 40 C./NMT 25% RH | 1 | 100.8% | 93.1% | 91.3% | 88.80% |
| | 3 | 101.1% | 54.5% | 16.3% | 7.5%, 6.0% |
| −20 C./Ambient RH | 1 | IP | IP | IP | IP |

TABLE 5

BAK Results

| | | Formulation | | | |
|---|---|---|---|---|---|
| | | EV06 Ophthalmic Solution, Placebo | EV06 Ophthalmic Solution, 10 mg/mL | EV06 Ophthalmic Solution, 30 mg/mL | EV06 Ophthalmic Solution, 40 mg/mL |
| | | | Lot Number | | |
| Specification | | BCL545-129A 80.0% to 120.0% | Lot BCL545-129B 80.0% to 120.0% | Lot BCL545-129C 80.0% to 120.0% | Lot BCL545-129D 80.0% to 120.0% |
| 5 C./Ambient RH | 0 | 96.9% | 94.4% | 95.0% | 95.6% |
| | 1 | 96.3% | 93.4% | 94.5% | 96.0% |
| | 3 | 96.5% | 93.5% | 93.5% | 94.3% |
| 25 C./40% RH | 1 | 96.6% | 94.4% | 94.3% | 95.9% |
| | 3 | 96.6% | 93.1% | 93.5% | 93.6% |

TABLE 5-continued

BAK Results

| | | Formulation | | | |
|---|---|---|---|---|---|
| | | EV06 Ophthalmic Solution, Placebo | EV06 Ophthalmic Solution, 10 mg/mL | EV06 Ophthalmic Solution, 30 mg/mL | EV06 Ophthalmic Solution, 40 mg/mL |
| | | | | Lot Number | |
| Specification | | BCL545-129A 80.0% to 120.0% | Lot BCL545-129B 80.0% to 120.0% | Lot BCL545-129C 80.0% to 120.0% | Lot BCL545-129D 80.0% to 120.0% |
| 40 C./NMT 25% RH | 1 | 98.2% | 94.0% | 92.8% | 94.8% |
| | 3 | 96.4% | 94.0% | 38.3% | 164.5% |
| −20 C./Ambient RH | 1 | | | | |

TABLE 6 pH Results

| | | Formulation | | | |
|---|---|---|---|---|---|
| | | EV06 Ophthalmic Solution, Placebo | EV06 Ophthalmic Solution, 10 mg/mL | EV06 Ophthalmic Solution, 30 mg/mL | EV06 Ophthalmic Solution, 40 mg/mL |
| | | | | Lot Number | |
| Specification | | BCL545-129A 4.0 to 5.0 | Lot BCL545-129B 4.0 to 5.0 | Lot BCL545-129C 4.0 to 5.0 | Lot BCL545-129D 4.0 to 5.0 |
| 5 C./Ambient RH | 0 | 4.6 | 4.6 | 4.5 | 4.5 |
| | 1 | 4.6 | 4.5 | 4.9 | 4.4 |
| | 3 | 4.6 | 4.5 | 4.5 | 4.4 |
| 25 C./40% RH | 1 | 4.5 | 4.5 | 4.4 | 4.3 |
| | 3 | 4.7 | 4.7 | 4.6 | 4.1 |
| 40 C./NMT 25% RH | 1 | 4.5 | 4.3 | 4.2 | 4.1 |
| | 3 | 4.6 | 4.5 | 4.7 | 3.8 |
| −20 C./Ambient RH | 1 | 4.6 | 4.4 | 4.4 | 4.3 |

TABLE 7

LACE Potency Results

| | | Test Article Number | | | | | |
|---|---|---|---|---|---|---|---|
| | | STA-000, 325 | | STA-000, 326 | | STA-000, 327 | |
| | | | | Formulation | | | |
| | | EV06 Ophthalmic Solution, 10 mg/mL | | EV06 Ophthalmic Solution, 30 mg/mL | | EV06 Ophthalmic Solution, 40 mg/mL | |
| | | | | Lot Number | | | |
| | | Lot BCL545-129B | | Lot BCL545-129C | | Lot BCL545-129D | |
| | | | | Specification | | | |
| | | 90.0% to 110.0% of Initial | | 90.0% to 110.0% of Initial | | 90.0% to 110.0% of Initial | |
| | | | | Results | | | |
| | | % of Label Claim | % of Initial | % of Label Claim | % of Initial | % of Label Claim | % of Initial |
| 5 C./Ambient RH | 0 | 98.1% | N/A | 94.0% | N/A | 91.5% | N/A |
| | 1 | 98.9% | 100.8% | 98.0% | 104.3% | 100.8% | 110.2% |
| | 3 | 99.4% | 101.3% | 95.9% | 102.0% | 94.5% | 103.3% |
| 25 C./40% RB | 1 | 102.2% | 104.2% | 97.3% | 103.5% | 98.4% | 107.5% |
| | 3 | 94.2% | 96.0% | 92.8% | 98.7% | 89.8% | 98.1% |
| 40 C./NMT 25% RH | 1 | 93.5% | 95.3% | 92.5% | 98.4% | 94.2% | 103.0% |
| | 3 | 79.3% | 80.8% | 73.6% | 78.3% | 68.1% | 74.4% |
| −20 C./Ambient RH | 1 | 92.3% | 94.1% | 91.6% | 97.4% | 80.0% | 87.4% |

TABLE 8

Appearance Results

| | | | Formulation | | |
|---|---|---|---|---|---|
| | | EV06 Ophthalmic Solution, Placebo | EV06 Ophthalmic Solution, 10 mg/mL | EV06 Ophthalmic Solution, 30 mg/mL | EV06 Ophthalmic Solution, 40 mg/mL |
| | | | Lot Number | | |
| Specification | | BCL545-129A Clear, colorless solution | Lot BCL545-129B Clear, colorless to yellow Solution | Lot BCL545-129C Clear, colorless to yellow Solution | Lot BCL545-129D Clear, colorless to yellow Solution |
| 5 C./Ambient RH | 0 | Clear, colorless solution | Clear, yellow solution Munsell: 5Y 9/1 | Clear, yellow solution Munsell: 5Y 9/2 | Clear, yellow solution Munsell: 5Y 9/2 |
| | 1 | Clear, colorless Solution 99.9% T at 500 nm | Clear, slightly yellow Solution 99.7% T at 500 nm Munsell: 10YR9/0.5 | Clear, slightly yellow Solution 98.7% T at 500 nm Munsell: 5Y9/1 | Clear, slightly yellow Solution 98.0% T at 500 nm Munsell: 5Y9/1.5 |
| | 3 | Clear, colorless solution 100.6% T | Clear, slightly yellow Solution 100.1% T Munsell: 10YR9/0.5 | Clear, slightly yellow Solution 99.5% T Munsell: 5Y9/1 | Clear, slightly yellow Solution 99.1% T Munsell: 5Y9/1 |
| 25 C./40% RH | 1 | Clear, colorless Solution 100.1% T at 500 nm | Clear, slightly yellow Solution 99.7% T at 500 nm Munsell: 10YR9/0.5 | Clear, slightly yellow Solution 98.7% T at 500 nm Munsell: 5Y9/1 | Clear, slightly yellow Solution 98.9% T at 500 nm Munsell: 5Y9/1.5 |
| | 3 | Clear, colorless solution 100.7% T | Clear, slightly yellow Solution 100.3% T at 500 nm Munsell: 10YR9/0.5 | Clear, slightly yellow Solution 99.7% T Munsell: 10YR9/1 | Clear, slightly yellow Solution 99.3% T Munsell: 5Y9/1 |
| 40 C./NMT 25% RH | 1 | Clear, colorless Solution 99.8% T at 500 nm | Clear, slightly yellow Solution 99.6% T at 500 nm Munsell: 10YR9/0.5 | Clear, slightly yellow Solution 99.1% T at 500 nm Munsell: 5Y9/1 | Clear, slightly yellow Solution 98.1% T at 500 nm Munsell: 5Y9/1.5 |
| | 3 | Clear, colorless solution 100.6% T | Clear, slightly yellow Solution 100.1% T Munsell: 10YR9/1 | Clear, slightly yellow Solution 13.4% T Munsell: 5Y9/1 | turbid, slightly yellow Solution 3.0% T Munsell: 5Y9/1 |
| −20 C./Ambient RH | 1 | Clear, colorless solution 99.6% T | Clear, pale yellow Solution 98.4% T at 500 nm Munsell: 5Y 9/0.5 | Clear, pale yellow Solution 96.3% T at 500 nm Munsell: 5Y 9/1 | Clear, pale yellow Solution 96.8% T at 500 nm Munsell: 5Y 9/1 |

TABLE 9A

Drug Related Impurities in Control Solution

Lot Number BCL545-129A
Specification
Report RRT of each individual impurity ≥0.05%
Report Total

| | | 0.65-0.66 | 0.67-0.68 | 0.68 | 0.80-0.81 | 1.08-1.09 | 1.12 | 1.17 | 1.19 | 1.21-1.22 | 1.29 | Total |
|---|---|---|---|---|---|---|---|---|---|---|---|---|
| 5 C./Ambient RH | 0 | | | | | | | | | | | |
| | 1 | | | | | | | | | | | |
| | 3 | ND | ND | ND | ND | ND | ND | ND | ND | ND | 0.08% | 0.08% |
| 25 C./40% RH | 1 | | | | | | | | | | | |
| | 3 | | | | | | | | | | | |
| 40 C./NMT 25% RH | 1 | | | | | | | | | | | |
| | 3 | ND | ND | ND | 0.15% | ND | ND | ND | ND | ND | ND | 0.15% |

TABLE 9B

Drug Related Impurities in 1% LACE Solution

Lot Number
Lot BCL545-129B
Specification
Report RRT of each individual impurity ≥0.05%
Report Total

|  |  | 0.65-0.66 | 0.67-0.68 | 0.68-0.69 | 0.80-0.81 | 1.08-1.09 | 1.12-1.14 | 1.17 | 1.19 | 1.20-1.22 | 1.29 | Total |
|---|---|---|---|---|---|---|---|---|---|---|---|---|
| 5 C./Ambient RH | 0 | 0.44% | 0.38% | ND | ND | 0.13% | ND | ND | ND | ND | ND | 0.95% |
|  | 1 | 0.65% | 0.25% | 0.42% | ND | 0.33% | ND | ND | ND | 0.05% | ND | 1.70% |
|  | 3 | 1.68% | 1.36% | ND | 0.14% | ND | 0.89% | ND | ND | 0.24% | ND | 4.31% |
| 25 C./ | 1 | 1.48% | 0.15% | ND | ND | 0.82% | ND | ND | ND | ND | ND | 2.45% |
| 40% RH | 3 | 1.46% | 1.57% | ND | ND | 0.09% | 2.49% | ND | ND | 0.30% | ND | 5.91% |
| 40 C./NMT 25% | 1 | 4.26% | 0.22% | 0.10% | ND | 2.59% | ND | ND | ND | 0.06% | ND | 7.23% |
| RH | 3 | 4.23% | 1.85% | ND | ND | 0.27% | 7.25% | ND | ND | 0.37% | ND | 13.97% |
| −20 C./Ambient RH | 1 | ND | 0.34% | 0.06% | ND | ND | 0.49% | ND | ND | 0.11% | ND | 1.00% |

TABLE 9C

Drug Related Impurities in 3% LACE Solution

Lot Number
Lot BCL545-129C
Specification
Report RRT of each individual impurity ≥0.05%
Report Total

|  |  | 0.65-0.66 | 0.67-0.68 | 0.68-0.69 | 0.80-0.81 | 1.08-1.09 | 1.12-1.14 | 1.17 | 1.19 | 1.20-1.22 | 1.29 | Total |
|---|---|---|---|---|---|---|---|---|---|---|---|---|
| 5 C./Ambient RH | 0 | 0.24% | 0.31% | ND | ND | 0.11% | ND | ND | ND | ND | ND | 0.66% |
|  | 1 | 0.56% | 0.12% | 0.11% | ND | 0.30% | ND | ND | ND | 0.05% | ND | 1.14% |
|  | 3 | 0.54% | 1.20% | ND | ND | ND | 0.69% | ND | ND | 0.27% | ND | 2.70% |
| 25 C./ | 1 | 1.40% | 0.14% | ND | ND | 0.83% | ND | ND | ND | ND | ND | 2.37% |
| 40% RH | 3 | 1.28% | 1.10% | ND | ND | ND | 1.56% | ND | ND | 0.16% | ND | 4.10% |
| 40 C./NMT 25% | 1 | 3.97% | 0.14% | ND | ND | 2.75% | ND | ND | ND | ND | ND | 6.86% |
| RH | 3 | 3.56% | 0.81% | ND | 0.09% | ND | 3.10% | ND | ND | 0.13% | ND | 7.69% |
| −20 C./Ambient RH | 1 | 0.06% | 0.30% | 0.08% | ND | ND | 0.28% | ND | ND | 0.10% | ND | 0.81% |

TABLE 9D

Drug Related Impurities in 4% LACE Solution

Lot Number
Lot BCL545-129D
Specification
Report RRT of each individual impurity ≥0.05%
Report Total

|  |  | 0.65-0.66 | 0.67-0.68 | 0.68-0.69 | 0.80-0.81 | 1.08-1.09 | 1.12-1.14 | 1.17 | 1.19 | 1.20-1.22 | 1.29 | Total |
|---|---|---|---|---|---|---|---|---|---|---|---|---|
| 5 C./Ambient RH | 0 | 0.21% | 0.28% | ND | ND | 0.11% | ND | ND | ND | ND | ND | 0.60% |
|  | 1 | 0.53% | 0.17% | ND | ND | 0.33% | ND | ND | ND | 0.10% | ND | 1.13% |
|  | 3 | 0.47% | 1.13% | ND | 0.14% | 0.24% | 0.57% | 0.05% | 0.05% | 0.11% | ND | 2.76% |
| 25 C./ | 1 | 1.32% | 0.15% | ND | ND | 0.78% | ND | ND | ND | ND | ND | 2.25% |
| 40% RH | 3 | 1.25% | 1.01% | ND | 0.14% | 0.14% | 1.07% | ND | ND | 0.13% | ND | 3.74% |
| 40 C./NMT 25% | 1 | 3.72% | 0.16% | ND | ND | 2.67% | ND | ND | ND | ND | ND | 6.55% |
| RH | 3 | 3.20% | 0.63% | ND | 0.06% | 0.22% | 2.62% | ND | ND | 0.09% | ND | 6.82% |
| −20 C./Ambient RH | 1 | ND | 0.27% | 0.05% | ND | ND | 0.39% | ND | ND | 0.08% | ND | 0.80% |

Example 5

DIOPTIN™ (Lipoic Acid Choline Ester) Eye Drop Reduces Mouse Lens Elasticity Methods In vitro test: Eight month old mouse lenses (C57BL/6J) were incubated for 12 hours in medium supplemented with selected levels (0-500 µM) of lipoic acid (LA). Lens elasticity was measured using the coverslip method known. After elasticity measurements, lenses were homogenized in a dissociation medium containing alkylating agent 1 (free SH modification). The homogenate was filtered and the rinsed, resuspended, retentate was treated with reducing agent (TCEP) and alkylating agent 2 (S-S SHs modified). After filtration and rinses, the levels of alkylated SH groups in retentate 2 was determined. Bovine serum albumin was the positive control for the sulfhydryl analysis.

In vivo test: Eight month old C57BL/6J mice were treated with 2.5 uL of a formulation of 5% LACE (DIOPTIN™, lipoic acid choline ester) three times per day at eight hour intervals in the right eye (OD) for 5 weeks. After the final treatment, lenses were removed and placed in a cuvette containing HBSS. Elasticity was determined with a computer controlled instrument that provided Z stage upward movements in 1 um increments with concomitant force measurements with a Harvard Apparatus F10 isometric force transducer. The elasticity of lenses from 8 week old C57BL/6J mice was determined for comparison.

Results

LA treatment led to a concentration-dependent decrease in lens protein disulfides concurrent with an increase in lens elasticity. Changes in disulfides and elasticity were negatively correlated (R=0.87, p=0.006). The $[LA]_{50}$ for both effects was 50±10 uM with maximal effect at 100 uM LA. After topical ocular treatment with DIOPTIN™ (lipoic acid choline ester) the lenses of the treated eyes of the old mice were more elastic than the lenses of untreated eyes, i.e. the relative force required for similar Z displacements was higher in the untreated eyes' lenses. In most instances the lenses of the treated eyes were even more elastic than the lenses of the 8 week old mice.

As the pen-central elasticity of the human lens decreases with age, humans lose the ability to accommodate. The results here suggest a topical ocular treatment that increases lens elasticity through reduction of disulfides will, concomitantly, restore accommodative amplitude.

Example 6

EV06 Draize Test for Eye Drop Ocular Safety

Safety of the EV06 was evaluated by the Draize test to evaluate its use at concentrations as high as 5%. The Draize Test is an acute toxicity test devised in 1944 by Food and Drug Administration (FDA) toxicologists John H. Draize and Jacob M. Spines. Initially used for testing cosmetics, the procedure involves applying 0.5 mL or 0.5 g of a test substance to the eye or skin of a restrained, conscious animal, and then leaving it for set amount of time before rinsing it out and recording its effects. Corneal, iris, and conjunctival responses were evaluated using the scale described by Draize et al., *J. Pharmacol. & Exp. Therapeutics*, 82:377-390 (1944)]. Because of the importance of the cornea to vision, 73% of the Draize score is based on corneal damage. A normal score was 0, increasing amounts of damage result in a higher score, with the maximum score possible being 110. A Draize score was computed at each observation time by averaging the total scores of all rabbits tested. Observations were made and recorded 24, 48, and 72 hours after treatment.

This test consists of instilling 30 to 50 µL of the product into one eye of 6 New Zealand white rabbits and monitoring to observe any abnormal clinical signs such as redness of conjunctiva, swelling, or increased blinking which may indicate irritation. The EV06 test concentrations (3%-5%) demonstrated no adverse effects (Draize Rabbit Eye test score of 2.0+/−0.6) and thus considered "not corrosive or irritating."

Example 7

DIOPTIN™ (Lipoic Acid Choline Ester) for Restoration of Accommodation in Presbyopes Methods Screening studies were conducted to determine the highest tolerated concentration when applied topically to rabbit eyes, in conjunction with bioanalysis of corneal, aqueous humor, and lens concentrations of EV06 and its metabolites. In a GLP rabbit study, animals were treated with topical 0, 1, 3 or 4% DIOPTIN™ (lipoic acid choline ester) solution three times daily for 90 consecutive days. Slit-lamp exams and fundoscopy were performed at pre-dose baseline and after 1, 30, and 90 days of dosing. Daily clinical observations, food consumption, body weights, clinical pathology, and toxicokinetics were performed. Full necropsy and ocular histopathology were also conducted.

Results

DIOPTIN™ (lipoic acid choline ester) ophthalmic formulations were well tolerated in rabbit eyes. No dose-related ocular signs of toxicity were observed at any timepoint in the GLP study. Ophthalmic exams were normal, with the exception of mild (1+) conjunctival congestion and (1+) discharge observed in some of animals dosed with 3% or 4% DIOPTIN™ (lipoic acid choline ester) on the first day of dosing, which persisted throughout the dosing period, but did not worsen. No systemic effects or adverse events were reported. Plasma levels of EV06 were at or below the limits of detection, indicating rapid metabolism.

DIOPTIN™ (lipoic acid choline ester) is a promising new treatment for presbyopia, with the potential to restore several diopters of accommodation. In preclinical studies, EV06 has been shown to be effective at increasing lens elasticity through reduction of lens protein disulfides. The ophthalmic formulation is non-irritating, and systemic and ocular safety have been demonstrated in a 90 day GLP ocular toxicology study at topical doses up to 4% three times daily.

Example 8

DIOPTIN™ (Lipoic Acid Choline Ester) Eye Drop to Treat Presbyopia: Corneal Penetration and Ocular Pharmacokinetics Methods Esters of lipoic acid were evaluated in rabbits for corneal penetration. Rabbits were also used to examine the metabolism, absorption, and distribution of LACE (LA prodrug) using HPLC-ESI/MS/MS (LOD>2 ng/ml).

Results

LACE was found to improve penetration over lipoic acid. A prototypic ocular eye drop formulation of LACE was tested as DIOPTIN™ (lipoic acid choline ester). It is rapidly degraded by endogenous butycholinesterases and provides elevated ocular tissue levels of LA. Lens DHLA (measured as LA) and LACE are both significantly elevated [P<0.05] using 3% DIOPTIN™ (lipoic acid choline ester) treated compared to untreated contralateral eye; 22.6+/−9.1(5) and 142.3+/−31.9 (5) nM/L, respectively.

Figure 2A:
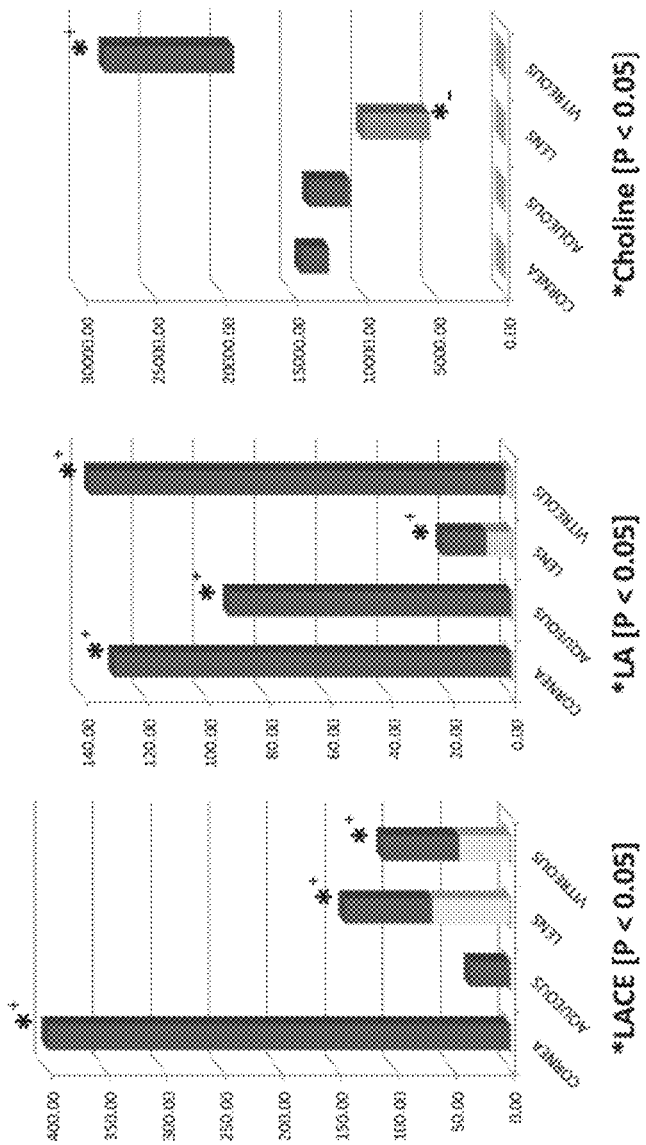
FIG. 2A shows lipoic acid choline ester metabolites distribution in rabbit eyes following treatment of the rabbit eyes each with 1 drop of a 3% lipoic acid choline ester formulation for 45 minutes.

As shown in FIG. 2A, DIOPTIN™ (lipoic acid choline ester) elevates LACE (prodrug) and LA (active) in ocular tissue samples (ESI/LC/MS/MS); importantly in the lens. LA can be cleared away in the form of 6,8-bismethylthio-octanoic acid (BMOA).

Figure 2B:
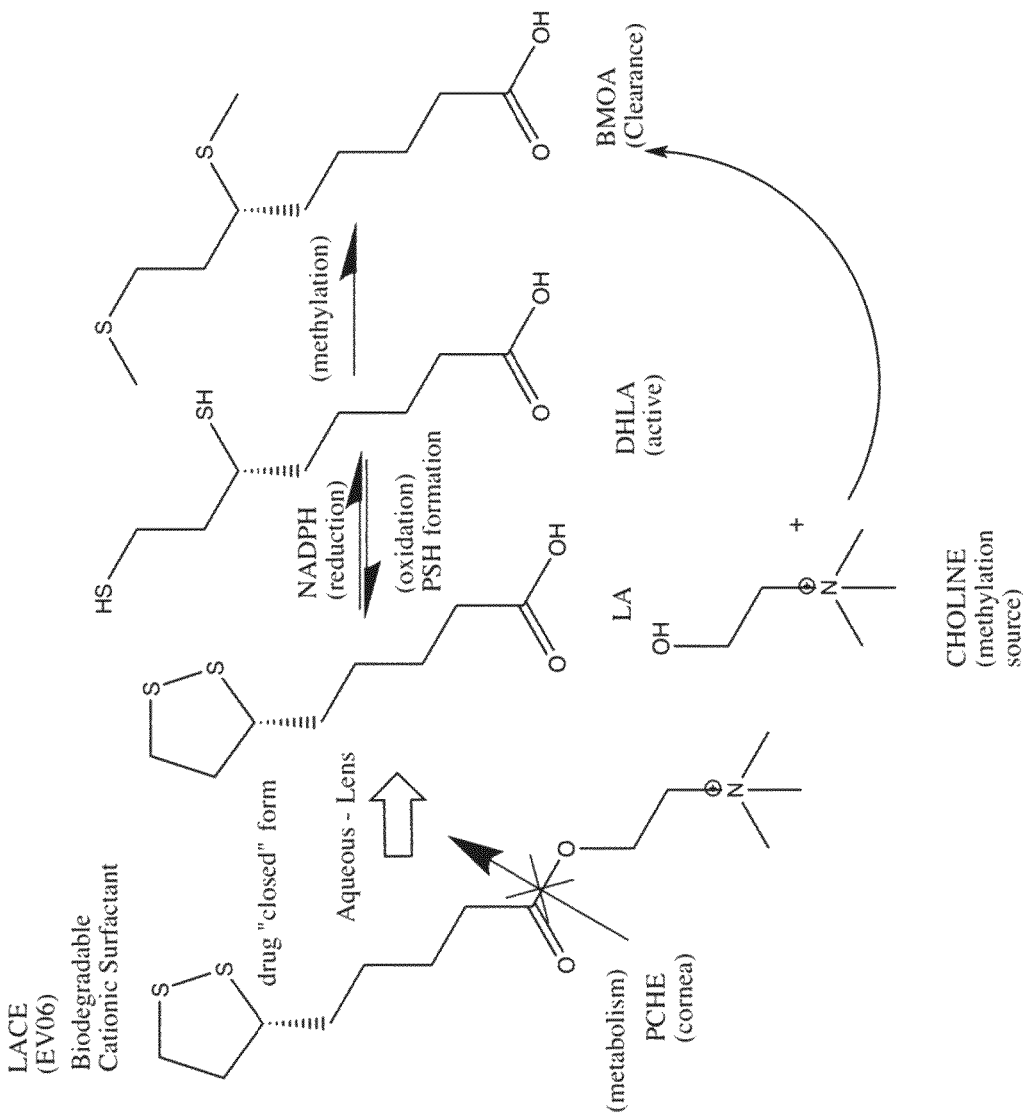
FIG. 2B is a schematic drawing of metabolism and clearance of lipoic acid choline ester.

A schematic showing of LACE metabolism is shown in FIG. 2B. The absorbed LACE molecule into the cornea is converted into non-surfactant natural products (lipoic acid and choline) in the cornea by pseudochlinesterases (PCHE), which minimizes corneal damage during transit into the aqueous. Importantly, this corneal cleavage process then allows for transfer of these intermediates into the aqueous. This rapid degradation into lipoic acid allows applying a higher concentration of LACE to an eye compared to that of a non-degradable cationic surfactants, for example, the safety limit for ocular use of BAK is <0.01%.

For comparison, in humans, the percent uptake (area under the curve or total over 4 hour period) is only 0.37% (Cagini) following application of lipoic acid formulation to the eyes; while separate animals studies (rabbits and mice) with EV06 formulation, 2.2% of the applied drop penetrates into the aqueous measured as LA. See FIG. 3.

In conclusion, DIOPTIN™ (lipoic acid choline ester) provides a convenient ocular delivery platform for improved aqueous delivery of a dithiol compound to reduce protein disulfides in order to soften the lens and restore accommodative amplitude, which is useful for treatment of Presbyopia.

Example 9

LACE Formulation with Glycerol

Lipoic acid choline ester was mixed in neat glycerol (no water) with brief heating to 80° C. for 8 hours. High concentrations of lipoic acid choline ester in a final clear solution were found. The final clear solution is stable.

Example 10

Single Bottle 2-Part Delivery System

A single bottle 2-part delivery system is described for the 2-part stable long-term manufactured formulation. This delivery bottle uses commercially available bottle, dropper tip, and cap. An insert is placed into the commercially available standard bottle (FIG. 4, left top), which separates the 2-parts until activation.
- Capacity: 4 mL; neck finish: 15-415
- Material: natural clear LDPE bottle with white cap
- Provides reliable repeatable dispensing of reagents; flexible contact-clear bottle permits easy content identification
- Excellent chemical resistance; material is suitable for most biotech diagnostic and pharmaceutical applications
- Delivers 40 μl drops (based on water; viscosity affects drop size) one at a time
- Manufacturer: Thermo Fisher Nalgene®
- Manufacturer Part No: 2750-9125

Composition of Part 1 and Part 2 are shown in Table 10 below:

TABLE 10

Composition of Parts 1 and 2

| LACE 3.00% Part 1 | | |
|---|---|---|
| LACE/glycerol | 1454 | mg/ml |
| LACE | 150 | mg |
| glycerol | 130 | mg |
| glycerol | 0.103 | ml |
| PART 2 ml 5 | | |
| alanine | 12.5 | mg |
| BAK | 0.35 | mg |
| PARTS 1 + 2 "ACTIVATED" | | |
| | mg/ml | % |
| LACE | 30.00 | 3.00% |
| glycerol | 26.00 | 2.60% |
| alanine | 2.50 | 0.250% |
| BAK | 0.07 | 0.007% |

Preparation of Part 1

150 mg of solid lipoic acid choline ester chloride is placed into 103 uL of medical grade glycerol and heated at 80° C. for 6 hours. An amorphous micelle is formed.

The insert shown in FIG. 4 (left drawing) has the following assembly components: the main insert stationary holder 1; the inner tube 2 that contains the non-hydrolytic solvent and also contains a filter to remove particulates; the lower seal 3 that contains the liquid within the inner tube; and the dropper tip 5 for sealing the insert prior to sterilization. The active agent in part-1 composition is added to the inner tube 2, as shown in 4. The dropper tip is then placed. Part 1 is sterilized using gamma-irradiation.

Assembling Parts 1 and 2

Part-2 contains the aqueous solution that is separately sterilized. Once the insert and aqueous solution are properly sterilized, they are combined (cap removed) under a sterile controlled manufacturing environment (FIG. 4, middle drawing). Part-1 insert is placed into the Part-2 container. Once assembled, long-term storage is possible without need for carefully controlled temperature conditions (<45° C.).

Activation

As shown in FIG. 4 (right drawing), to activate, the patient only needs to compress or "squeeze" the bottle to release part-1 into part-2 aqueous solution. This step moves the lower seal 3 (FIG. 4) upward to expose the inner tube 2 (FIG. 4) perforations. Part-1 composition then flows into part-2 aqueous solution. The solution is readily dissolved with brief shaking. The lid is still in place during activation. The final formulation (about 5 mL) contains:
3% Lipoic Acid Choline Ester;
0.01% Benzalkonium Chloride;
2.7% Glycerin, USP; and
0.5% Alanine, USP;
with a pH of 4.5±0.2.

This provides sufficient formulation for a BID 60-day treatment (40 uL/drop).

The final formulation is sufficiently stable to maintain predicted outcome. The final formulation is stable when refrigerated (5° C.) for 30 days without degradation >0.5% of the active compound.

Parts 1 and 2 maintained in the 2-part bottle provides a long-term shelf life resistant to thermal degradation <45° C. for 2 years.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

All of the various aspects, embodiments, and options described herein can be combined in any and all variations.

All publications, patents, and patent applications mentioned in this specification are herein incorporated by reference to the same extent as if each individual publication, patent, or patent application was specifically and individually indicated to be incorporated by reference.

What is claimed:

1. A pharmaceutical composition comprising:
   (a) lipoic acid choline ester at a concentration of 1%, 1.5%, 3%, or 4% by weight of the composition;
   (b) a preservative at a concentration of 0.005% to 0.1% by weight of the composition;
   (c) having a pH of 4 to 6 in an aqueous solution;
   (d) a biochemical energy source at a concentration of 0.1% to 5% by weight of the composition; and
   (e) a non-aqueous excipient glycerol at a concentration of 1% to 3% by weight of the composition; wherein the non-aqueous excipient glycerol is first mixed with lipoic acid choline ester to form a non-aqueous composition and the non-aqueous composition is then mixed with the aqueous solution; and wherein less than 2% of the lipoic acid choline ester is degraded following storage at 25° C. under 40% relative humidity for 3 months.

2. The pharmaceutical composition of claim 1, wherein the preservative is benzalkonium chloride and the biochemical energy source is alanine.

3. The pharmaceutical composition of claim 2, wherein the benzalkonium chloride is present at a concentration of about 0.01% w/v.

4. The pharmaceutical composition of claim 2, wherein the alanine is present at a concentration of 0.1% or 0.5% w/v.

5. The pharmaceutical composition of claim 1, wherein the lipoic acid choline ester has a counter ion selected from the group consisting of chloride, bromide, iodide, sulfate, methanesulfonate, nitrate, maleate, acetate, citrate, fumarate, hydrogen fumarate, tartrate, succinate, benzoate, and anion of glutamic acid.

6. The pharmaceutical composition of claim 1, further comprising a buffer.

7. The pharmaceutical composition of claim 6, wherein the buffer is selected from the group consisting of phosphate buffer, acetate buffer, citrate buffer, and borate buffer.

8. The pharmaceutical composition of claim 1, having a pH of 4.2 to 4.7.

9. The pharmaceutical composition of claim 1, consisting essentially of
   (a) lipoic acid choline ester at a concentration of 1%, 1.5%, 3%, or 4% by weight of the composition;
   (b) a preservative at a concentration of 0.005% to 0.1% by weight of the composition;
   (c) having a pH of 4.2 to 4.7 in an aqueous solution;
   (d) a biochemical energy source at a concentration of 0.1% to 5% by weight of the composition; and
   (e) a non-aqueous excipient glycerol at a concentration of 1% to 3% by weight of the composition; wherein the non-aqueous excipient glycerol is first mixed with lipoic acid choline ester to form a non-aqueous composition and the non-aqueous composition is then mixed with the aqueous solution; and wherein less than 2% of the lipoic acid choline ester is degraded following storage at 25° C. under 40% relative humidity for 3 months.

* * * * *